US011679078B1

(12) United States Patent
Stone et al.

(10) Patent No.: US 11,679,078 B1
(45) Date of Patent: *Jun. 20, 2023

(54) OPHTHALMIC FORMULATIONS AND RELATED METHODS

(71) Applicant: EternaTear, Inc., Raleigh, NC (US)

(72) Inventors: Ralph P. Stone, Fort Worth, TX (US); Timothy R. Willis, Raleigh, NC (US)

(73) Assignee: ETERNATEAR, INC., Raleigh, NC (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/689,212

(22) Filed: Mar. 8, 2022

(51) Int. Cl.
| A61P 27/04 | (2006.01) |
| A61K 9/00 | (2006.01) |
| A61K 47/24 | (2006.01) |
| A61K 47/44 | (2017.01) |
| A61K 9/107 | (2006.01) |

(52) U.S. Cl.
CPC .......... *A61K 9/0048* (2013.01); *A61K 9/1075* (2013.01); *A61K 47/24* (2013.01); *A61K 47/44* (2013.01); *A61P 27/04* (2018.01)

(58) Field of Classification Search
CPC ....... A61P 27/04; A61K 9/0048; A61K 47/24; A61K 47/44; A61K 9/1075
See application file for complete search history.

(56) References Cited

U.S. PATENT DOCUMENTS

| 4,151,001 | A | 4/1979 | Anderson et al. |
| 4,421,748 | A | 12/1983 | Trager et al. |
| 4,914,088 | A | 4/1990 | Glonek et al. |
| 5,252,246 | A | 10/1993 | Ding et al. |
| 5,278,151 | A * | 1/1994 | Korb .................... A61K 31/685 514/76 |
| 5,294,607 | A | 3/1994 | Glonek et al. |
| 5,371,108 | A | 12/1994 | Korb et al. |
| 5,578,586 | A | 11/1996 | Glonek et al. |
| 5,672,358 | A | 9/1997 | Tabibi |
| 5,942,558 | A | 8/1999 | Korb et al. |
| 6,436,429 | B1 | 8/2002 | Peyman |
| 8,591,033 | B2 | 11/2013 | Korb et al. |
| 8,746,883 | B2 | 6/2014 | Korb et al. |
| 8,915,592 | B2 | 12/2014 | Korb et al. |
| 9,044,388 | B2 | 6/2015 | Korb et al. |
| 9,161,905 | B2 | 10/2015 | Korb et al. |
| 9,545,197 | B2 | 1/2017 | Korb et al. |
| 11,278,493 | B2 * | 3/2022 | Willis .................... A61K 47/44 |
| 2010/0086512 | A1 | 4/2010 | Schaefer |
| 2010/0247593 | A1 | 9/2010 | Wikberg |
| 2012/0128763 | A1 | 5/2012 | Maskin |
| 2013/0216596 | A1 | 8/2013 | Viladot Petit |
| 2014/0206764 | A1 | 7/2014 | Liu |
| 2015/0202306 | A1 | 7/2015 | Coffey |
| 2015/0297511 | A1 | 10/2015 | Xia |
| 2016/0199428 | A1 | 7/2016 | Simmons et al. |
| 2016/0338952 | A1 | 11/2016 | Ketelson |
| 2016/0354307 | A1 | 12/2016 | Hilliard |
| 2018/0008538 | A1 | 1/2018 | Izquierdo Torres |
| 2018/0325854 | A1 | 11/2018 | Coulon |
| 2020/0179281 | A1 * | 6/2020 | Willis .................... A61K 9/107 |

FOREIGN PATENT DOCUMENTS

| EP | 0 459 148 A2 | 12/1991 |
| EP | 0 535 545 | 7/1993 |
| WO | 2006004577 A2 | 1/2006 |
| WO | 2015055301 A1 | 4/2015 |
| WO | 2017074420 A1 | 5/2017 |
| WO | 2017132190 A1 | 8/2017 |

OTHER PUBLICATIONS

International Search Report for PCT/US2019/065191, dated Mar. 19, 2020.
Wikipedia Contributors, "Beeswax," Wikipedia, accessed Sep. 27, 2018. Available at https://en.wikipedia.org/w/index.php?title=Beeswax &oldid=861444220, 7 pages.
Wikipedia Contributors, "Eye Drop," Wikipedia, accessed Sep. 13, 2018. Available at https://en.wikipedia.org/w/index.php?title=Beeswax &oldid=847772327, 4 pages.
Wikipedia Contributors, "Surfactant," Wikipedia, accessed Sep. 13, 2018, 11:50 UTC. Available at https://en.wikipedia.org/w/index. php?title=Beeswax&oldid=858602819, 11 pages.
Freeman, P. David, and Kahook, Malik Y. "Preservatives in Topical Ophthalmic Medications: Historical and Clinical Perspectives." Expert Rev Ophthalmol. 2009;4(1):59-64. Expert Reviews Ltd., London.
Klier, John. "Microemulsions." In Kirk-Othmer Encyclopedia of Chemical Technology, John Wiley & Sons, Inc (Ed.), United States, dated Jul. 13, 2012, 22 pages.
Korb, Donald R. "Survey of Preferred Tests for Diagnosis of Tear Film and Dry Eye." Cornea, 19(4): 483-486 (2000), Lippincott Williams and Wilkins, Inc., Philadelphia.
Kostansek, Edward. "Emulsions." In Kirk-Othmer Encyclopedia of Chemical Technology, John Wiley & Sons, Inc (Ed.), United States, dated Jul. 12, 2012, 24 pages.
Lanigan, Rebecca S., and Yamarik, Torrill A. "Final Report on the Safety Assessment of PEG-6, -8, and -20 Sorbitan Beeswax." Int. J. Toxicology, 20(Supp. 4):27-38 (2001). Cosmetic Ingredient Review Panel, SAGE Publishing, United States.
Leray, Claude. "Waxes." In Kirk-Othmer Encyclopedia of Chemical Technology, John Wiley & Sons, Inc (Ed.), United States, dated Sep. 15, 2016, 25 pages.
Moshirfar, Majid et al. "Artificial tears potpourri: A literature review." Clinical Ophthalmology, vol. 2014 (8):1419-1433 (2014), Dove Press, United States.

(Continued)

*Primary Examiner* — Sean M Basquill
(74) *Attorney, Agent, or Firm* — Barnes & Thornburg LLP

(57) ABSTRACT

This disclosure is directed to ophthalmic suspensions for dry eye and other ocular indications that provide long-lasting on eye benefits. The disclosure provides methods of increasing lipid layer thickness and methods of lubricating an eye. The disclosure also provides methods of maintaining integrity of an eye's tear film layers which increases the eye's lipid layer thickness and methods of recreating or building one or more layers of an eye's tear film.

13 Claims, 1 Drawing Sheet

(56) References Cited

OTHER PUBLICATIONS

Patel, Ashaben et al. "Ocular drug deliver systems: An overview." World J Pharmacol., 2(2): 47-64 (2013). Baishideng Publishing Group Inc, United States.
Pucker, AD, NG, SM, and Nichols, JJ. "Over the counter (OTC) artificial tear drops for dry eye syndrome." Cochrane Database of Systematic Reviews, Issue 2. Art. No. CD009729 (2016). John Wiley & Sons, Ltd., United States.
Restasis MultiDose TM [product prescribing information]. Irvine, CA: Allergan; revised Oct. 2016.
Sweeney, Deborah F., et al. "Tear film stability: A review." Experimental Eye Research, 117, 28-38 (2013). Elsevier Ltd., United States.
Tadros, Tharwat. "Surfactants." In Kirk-Othmer Encyclopedia of Chemical Technology, John Wiley & Sons, Inc (Ed.), United States, dated Jul. 13, 2012, 46 pages.
Fisher Chemical—Fisher Scientific, product listing for "Mineral Oil, Light (NF/FCC), Fisher Chemical", [online] https://www.fishersci.com/shop/products/mineral-oil-light-nf-fcc-fisher-chemical-3/O1211 (Accessed May 13, 2021).
Fisher Chemical—Fisher Scientific, product listing for "Mineral Oil, Heavy (USP/FCC), Fisher Chemical", [online] https://www.fishersci.com/shop/products/mineral-oil-light-nf-fcc-fisher-chemical-2/O1211 (Accessed May 13, 2021).
Ding, Shulin, "Recent developments in ophthalmic drug delivery", PSTT (Nov. 8, 1998), vol. 1, No. 8, pp. 328-335.
Tamilvanan, S., et al., "The potential of lipid emulsion for ocular delivery of lipophilic drugs", European Journal of Pharmaceutics and Biopharmaceutics, (2004), vol. 58, pp. 357-368.

\* cited by examiner

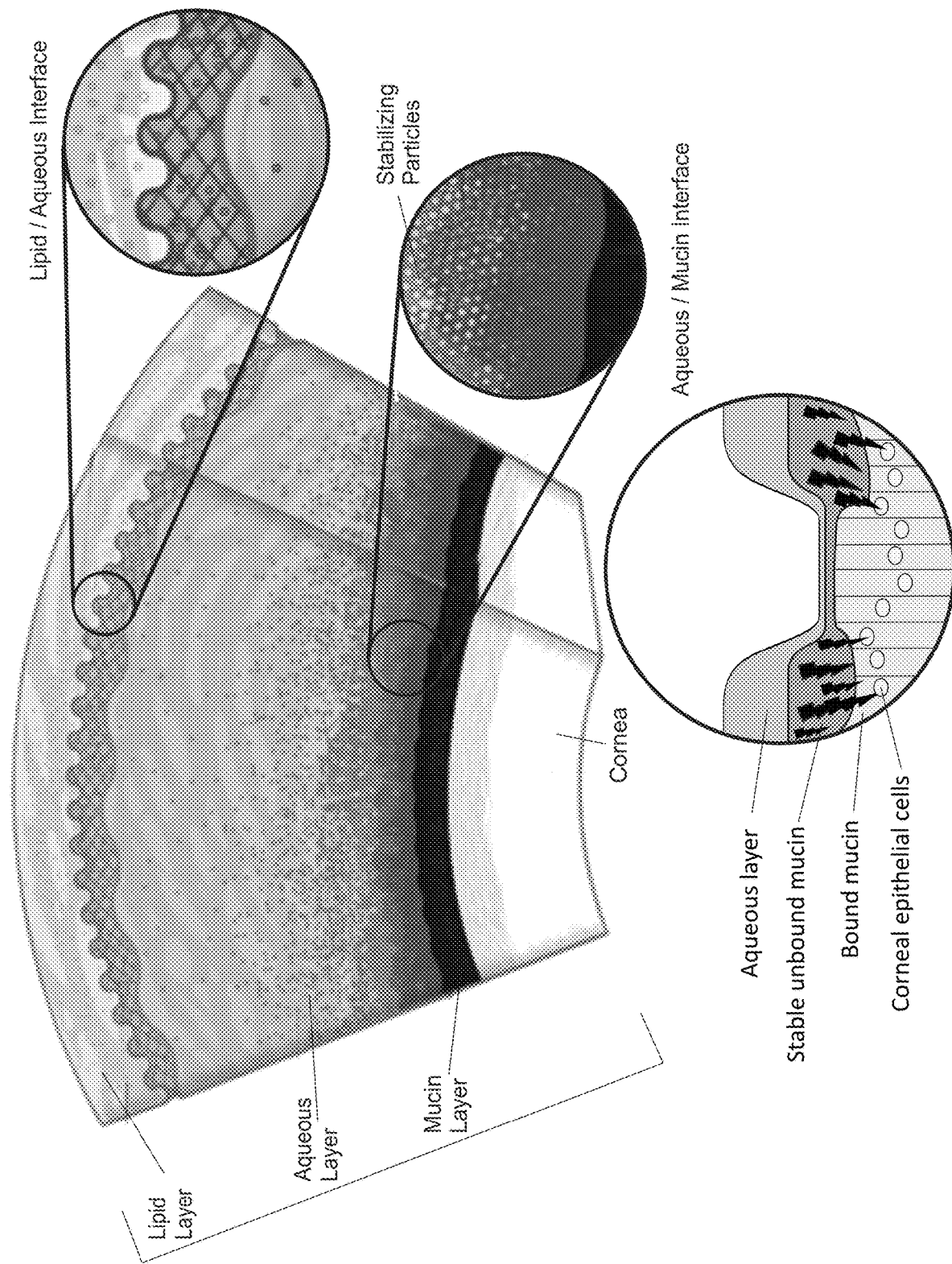

OPHTHALMIC FORMULATIONS AND RELATED METHODS

FIELD

The present disclosure provides a long-lasting ophthalmic suspension for ocular therapy for dry eye and other ocular indications. The ophthalmic suspension described herein provide relief for dry eye that lasts two to ten times longer on the eye than currently marketed products.

BACKGROUND

The tear film is produced by secretions of the different glands of the eye during normal blinking. These secretions or components makeup a healthy and stable tear film. The aqueous portion of the tear is produced by primarily the lacrimal gland activated by blinking. The external tear film layer is the lipid layer which is excreted during blinking primarily from the Meibomian glands located in the eye lids. The lipid layer provides a protective layer on top of the tear film designed to reduce the evaporation of the aqueous of the tear film. Thinning of the lipid layer adds increased evaporation of the aqueous layer resulting in a dry eye on the corneal surface between blinks. Such dry eye patients tear film rate of evaporation increases by 30% to 38% at less than 50% relative humidity These collective of secretions from the lacrimal and Meibomian glands along with eye lid providing a wiper effect from normal blinking provides a normal, long lasting, and stable ocular tear film. While the normal production of ingredients continually repair and replaces the tear film, the loss of key ingredients due to dysfunction or non-secretions makes the tear film unstable and rapidly leads to loss of the tear film structure resulting in dry eye.

The tear film protects, lubricates, nourishes and cleanses the ocular surface. An important role is to prevent dehydration of the underlying cornea and the tissue of the conjunctiva as well as to provide a lubricated surface during a blink. The tear film serves in a number of different functions. One of the most important functions of the tear film is its role reducing evaporation from the surface of the eye, thereby preventing corneal and conjunctival drying. Failure of the tear film to keep the eye adequately hydrated and lubricated can result in epithelial cell damage and inflammation. This, in turn may result in severe discomfort or pain and even severe corneal damage. The tear film lubricates the eyelids ensuring smooth and comfortable blinking. If the surface of the cornea and eyelid are not sufficiently smooth or lubricated, abrasive damage may result and cause similar problems of those of corneal and conjunctival drying as mentioned above and has been described as lid wiper epitheliopathy. Since the cornea is an avascular construct, the tear film contains nutrients to nourish the corneal epithelium and removes cellular waste products and debris. It also supplies oxygen to, and removes carbon dioxide from, the corneal and conjunctival epithelia. If the cornea becomes malnourished, blood vessels may grow into it in order to provide the necessary nutrients. These vessels can obstruct vision and are characteristic of very severe dry eye conditions.

The tear film contains antibacterial and anti-viral substances which defend the eye against infection. Tears are buffered and are able to neutralize mild acids and bases thereby enabling the eye to tolerate the instillation of substances with a pH range of 6.6 to 7.8. The tear film refracts (bends) light and aids visual acuity by forming a smooth, clear optical surface over the cornea (thereby eliminating minute surface irregularities in the corneal epithelium). The tear film has a refractive index ranging between 1.3345 and 1.3360 (compared was an Index of 1.0 for air).

The tear film is understood to be composed of five distinct layers where each perform a key function in maintaining the tear film. An outer (oily) lipid layer which lubricates the movement of the eye lid and reduces evaporation of the aqueous (watery) layer. The next layer that makes up the largest portion of the tear film is the aqueous (watery) layer that hydrates and provides nutrients to the avascular cornea while removing cellular by product and debris. Finally, an inner mucin layer excreted by the cornea that lowers the surface tension of the tear film to enable uniform spreading across the surface of the eye. An outer interstitial layer is located between the lipid layer and aqueous layer. An inner interstitial layer is located between the aqueous layer and mucin layer.

A continuous basal secretion of the tear components at all times of the day and night normally ensures the tear film provides adequate lubrication and protection for most environments. However, the production and maintenance of the tear film does not simply rely on the production of sufficient quantities of tears. The quality (i.e., the composition) of the tears and the blinking process also play an important role in maintaining a healthy tear film.

Normal tears with the correct balance of lipid, aqueous and mucin components combined during blinking form a stable and protective tear film. Between blinks, the tear film thins due to evaporation and lipid molecules from the outer layer begin to migrate through the aqueous layer towards the mucin layer. The aqueous portion of the tear also is exchanged on the eye approximately 16% by volume every minute where the lipid layer is exchanged at a rate of approximately 2% per minute on the eye. Contamination of the mucin layer by the lipid layer increases the surface tension of the tear film and eventually causes it to rupture (break-up) and bead up on the surface of the cornea forming a dry spot. A subsequent blink normally repairs this rupture by removing the lipid contaminants from the mucin layer and restoring a normal aqueous layer. Repeated rupture, however, can cause loss of the mucin layer and show staining when observed using fluorescein.

In the balance between the tear film components is upset as a result of aging, diseases, gland malfunction, drugs, preservatives in ophthalmic preparations or the wearing of contact lenses, failure to blink appropriately and lid closure or sealing issues the tear film becomes less stable and may break up in only a few seconds (i.e., before the next blink). When this occurs the break-up time is shorter than the interval blinks (whether because of an adequate tear film or inadequate blinking), dry spots develop on the ocular surface of the eye, and this becomes the first stage in the development of ocular surface disease or dry eye. Ideally the breakup time should equal or be longer that the normal blink interval.

Loss of the tear film structure leads to dry eye which is an ophthalmic medical condition currently exhibited in over 350 million patients worldwide, and over 50 million in the US: equivalent to 15% of the US population. The discomfort resulting from a dry eye condition may include ocular dryness, grittiness, burning, soreness, scratching, or foreign body reaction. The degree of discomfort is dependent upon the subject and the condition of the subject. The leading cause of dry eye comes from the loss of the lipid layer due to the dysfunction of the Meibomian glands estimated to be as high as 86% of all dry eye. Changes in the composition are reflected in the meibum being produced as a thick/semisolid material and/or the loss of the glands producing the meibum. Also, little is known about the importance of various constituents in the formation of the lipid layer although difference have been discussed by many authors. The importance of the lipid layer in the maintenance of the tear film is well studied showing that is critical in preventing the loss of the aqueous layer by evaporation. The thinning of the lipid layer is believed to enhance the symptoms of dry eye resulting from the evaporation of the aqueous component of the tear film.

The most common treatment for dry eye involves temporary alleviation of dry eye symptoms by topical application of an artificial tear substitute that provide a volume of liquid to the surface of the eye and neighboring tissues, e.g., eyelids, cornea. Typical commercially available tear substitute compositions comprise water soluble polymer solutions. Examples of such solutions include saline solutions of polyvinyl alcohol, hydroxypropylmethyl cellulose, or carboxymethyl cellulose. U.S. Pat. No. 4,421,748 teaches an artificial tear composition comprising an aqueous hypotonic solution of lecithin and a viscosity-adjusting agent such as a solution of a soluble cellulose. An aqueous tear film extends over the ocular surface and maintains a moist and lubricated ocular surface. It is also known that dehydration of moisture from the eye may result in discomfort. Further, compositions are available in the market intended for dry eye treatment. Commercially available compositions are primarily aqueous materials that supplement the tear film by adding a film of a water soluble polymer over the surface of the eye. These films are short lived and provide limited relief.

A number of improved compositions for dry eye treatment are disclosed in U.S. Pat. Nos. 4,914,088; 5,278,151; 5,294,607; 5,578,586, and 9,161,905, each incorporated herein by reference for its teaching of how to form an oil film over the surface of the eye including compositions and uses. U.S. Pat. No. 4,914,088 teaches the use of certain charged phospholipids for the treatment of dry eye symptoms. The addition of a charged phospholipid to the eye is believed to assist in replicating the tear film that would naturally occur in the eye. In accordance with the patent, the phospholipid composition, preferably in the form of an aqueous emulsion, is topically applied to the eye where it is believed to disperse over the ocular surface and form a film that replicates a lipid layer that would be formed by the spreading of a naturally occurring lipid excreted principally from the Meibomian glands during blinking. Because the phospholipid, when applied to the eye carries a net negative charge, it is believed that aligned molecules repel each other preventing complex aggregate formation thereby resulting in a stable phospholipid interface between the lipid and aqueous phase. The patent theorizes that the film formed from the charged phospholipid assists in the formation of a barrier film reducing evaporation of the aqueous layer, thereby preserving the tear film. Others have theorized that the phospholipid also functioned as a surfactant maintaining the emulsion stability.

The above referenced U.S. Pat. Nos. 5,278,151; 5,294,607; 5,578,586; 9,279,095; and 9,375,401 disclose additional improvements in dry eye treatment. In these patents, the dry eye treatment composition of U.S. Pat. No. 4,914,088 is improved by the addition of an oil to the eye treatment composition, preferably a non-polar oil such as mineral oil comprised of hydrocarbon ingredients. The oil is added to improve the performance of a dry eye treatment composition by increasing the longevity of the tear film formed on the eye as a consequence of the formation of an oil film over the ocular surface that functions as an evaporation barrier—i.e., by providing and/or thickening the dehydration barrier (the oil layer) on the outer surface of the tear film. Thus, the oil increases the efficacy of the dry eye treatment solution and reduces performance variability from subject to subject. It also supplements the oils provided from the Meibomian gland which in many cases of dry eye does not provide sufficient oils to provide an adequate lipid tear layer. A preferred embodiment disclosed in the above referenced patents is a dry eye treatment composition comprising a meta stable oil-in-water emulsion where the water phase includes the charged phospholipid believed to function both as an emulsifier and as a surfactant that assists in spreading of the oil over the eye to form a non-blurring film bonding of the oil to the aqueous layer of the tear film. The emulsion is desirably "meta" stable so that when the emulsion is applied to the eye, it will rapidly break and spread over the ocular surface when it first comes into contact with the ocular environment.

U.S. Pat. Nos. 5,371,108, 5,278,151 and U.S. Patent Publication No 2016/03389952 to Korb teach a method or formulation for creating an emulsion or gel comprising oil and wax to form a tear film on the ocular surface to prolong the residence time of oil. The wax-containing gel has not, however, been produced and marketed commercially because of the difficulty in homogenizing the wax in such a way that does not induce visual blurring beyond what would be acceptable by most consumers. Specifically, autoclaving to sterilize the wax-containing formulation leads to increased particle size which leads to irritation and blurred vision. Gels are semi-solid formulations with high viscosity. In contrast, the present disclosure is directed to metastable emulsions that behave as flowing liquids at room temperature. Emulsions behave as liquids and as such do not exhibit a static internal structure or have high viscosity. Korb also utilizes preservatives at levels that are known to be toxic to cornea cells upon administration and does not disclose a vehicle that would exhibit a long lasting dwell time A number of ophthalmic formulations and compositions of use note the use of Zeta potential and are disclosed in WO2016209555, WO2015057847, WO2011098578, WO2011084509, WO03053405, US2012328702, US2012225834, and U.S. Pat. Nos. 7,060,285, 9,827,191, 8,298,569, 7,893,040, 7,834,172, and 10,137,083 each incorporated herein by reference for its teaching of the use of Zeta potential.

Current commercially available products, including oil and water emulsion products, often supplement one or more layers of the tear film through various combinations of oils, aqueous solutions, and mucomimetics. These lipid emulsions provide sufficient lubrication and prevention against desiccation, but they remain inadequate in terms of their ability to remain on the eye and provide lasting relief, which is the most desired clinical result. Additionally, these compositions fail to fully rebuild the tear film, causing the layers to lose their natural stability on the surface of the eye and thus have limited relief due to their on-eye dwell time being less than 30 minutes. Without connectivity to each subsequent layer of the film, the lipid, aqueous, and mucin layers, whether natural, artificial or some combination thereof, tend to be expressed in a period of time too short to provide lasting comfort from the symptoms of dry eye. FIG. 1 provides an enlarged view of the eye and the components of the layers and interfaces of the tear film. The normal tear film is 3-6 µM thick. The two insets with lines to the tear film show enlarged views of the lipid/aqueous interface and the aqueous/mucin interface. The third inset shows the thinning of the layers and interfaces associated with dry eye. In particular, it shows the thinning of (i) the aqueous layer, (ii) the unbound mucin layer, and (iii) the bound mucin layer on the surface of the corneal epithelial cells. Existing products do not stabilize the different layers and interfaces of the tear film including the lipid layer. Thus, the existing products do not create a stable lipid layer and provide long term benefits.

SUMMARY OF THE DISCLOSURE

The human eye's tear film includes the three distinct layers and recent learning and research has determined that there are two additional layers of the tear film being interstitial layers. These interstitial layers of the tear film are from other glands in the eyelid different from the lachrymal and Meibomian Gland of the eyelid. These interstitial layers excrete ingredients that provide a healthy, normal, and stable tear film. These glands include the glands of Krause, Wolfring, Moll and Heine that excrete wax, wax esters as well as additional surfactants and chemical agents that enhance the Velcro effect of the interface between the tear film layers as well as build and thicken the tear film to reduce tear film evaporation. The two interstitial layers, each perform a key function in maintaining the tear film. In total, the tear film incorporates five layers with the outer (oily) lipid layer excreted by the Meibomian gland. The first interstitial layer is excreted by the Meibomian gland and glands of Wolfring, Krause, Moll and Heine include anionic polar phospholipids (i.e., connects the lipid layer to the aqueous layer), wax esters and surfactants (i.e., thickens and enhances the lipid layer and interstitial attachment) that connect the lipid layer to the aqueous layer of the tear film to maintain a stable tear film. The next layer that makes up the largest portion of the tear film is the aqueous (watery) layer that hydrates and provides nutrients to the avascular cornea while removing cellular by product and debris. The second interstitial layer excreted by the glands of Wolfring, Krause, Moll and Heine is made of wax esters and surfactants that thicken the aqueous and enhance the connection to the corneal secreted mucin which connects the aqueous layer to the cornea to maintain a stable tear film. Finally, an inner mucin layer excreted by the cornea is attached to the cornea and lowers the surface tension of the tear film to enable uniform spreading of the tear film across the surface of the eye. The wax and wax esters as well as surfactants and other agents that, in combination with the Meibomian gland that excrete lipids, and the lachrymal gland aqueous secretions with lip wiper effect of the eyelid due to normal blinking action, builds a normal, stable and long lasting ocular tear film. Thus, the addition of wax esters and their partial hydrolysis products, such as beeswax and its normal distribution throughout the various phases of the suspension has the same effect of improving the efficacy of the composition by allowing the lubricating elements to remain on the eye for an extended period of time similar to a normal tear film.

Disclosed herein are ophthalmic suspensions that mimic natural tear film including the three distinct layers and the two interstitial layers to rebuild or otherwise increase the thickness of the eye's lipid layer for an extended period thereby reducing tear film evaporation and maintaining a normal ocular tear structure in the eye. The ophthalmic suspensions provided herein may perform as substitutes for each tear film layer (lipid, aqueous, interstitials and mucin) that enhance the tear film, improving the tear film's natural function to create significantly longer lasting on eye residence time and improved patient comfort. By providing a longer lasting effect on the eye, fewer applications or drops are required to be used by a patient in need of treatment. By substituting the lipid (outer) layer, enhancing the aqueous (middle) layer, mimicking the mucin (inner) layer and incorporating the interstitial layers, the present ophthalmic suspensions mimic the natural tears and perform as authentic artificial tears.

Ophthalmic suspensions are provided that include emulsified oil-in-water suspensions that contain wax esters, or a suitable combination of wax esters, surfactants and other components as provided herein that mimic the body's natural tear film as well as provide a tear film that maintains its structure on the eye for extended periods of time.

According to one aspect, the present disclosure provides an ophthalmic suspension that includes: i) an aqueous phase comprising water and one or more components selected from the group consisting of at least one wax ester, at least one anionic polar surfactant, at least one nonionic surfactant, at least one salt, and at least one phosphate; and ii) an oil phase comprising at least one mineral oil and, optionally, at least one wax ester. According to one embodiment, the wax ester exhibits a mean particle size that is determined via a Microtrac particle analyzer. The wax ester exhibits a mean particle size of at least about 2.0 microns. According to one embodiment, the wax ester exhibits a mean particle size distribution of at least about 2.0 microns to about 20.0 microns. According to one embodiment, the wax ester exhibits a mean particle size distribution of at least about 5.0 microns. According to one embodiment, the ophthalmic suspension has an osmolality of from about 245 mOsmol/kg to about 315 mOsmol/kg. According to one embodiment, the ophthalmic suspension is formulated as a free flowing emulsified suspension at about 30° C. According to one embodiment, the wax ester is present in a concentration of about 0.8 weight percent to about 1.2 weight percent. According to one embodiment, the wax ester is a natural beeswax. According to one embodiment, the wax ester is a synthetic beeswax. According to one embodiment, the ophthalmic suspension exhibits a negative zeta potential of from about −60 mV to about −110 mV. According to one embodiment, the ophthalmic suspension exhibits an ionic mobility of from about −5.9 (µms)/(V/cm) to about −7.4 (µms)/(V/cm). According to one embodiment, the oil is a mixture of a lightweight mineral oil and a heavy weight mineral oil. According to one embodiment, the lightweight mineral oil exhibits a kinetic viscosity of from about 3.0 $mm^2s^{-1}$ to about 34.4 $mm^2s^{-1}$ at 40° C. and the heavy weight mineral oil exhibits a viscosity of kinetic viscosity of from about 34.5 $mm^2s^{-1}$ to about 150 $mm^2s^{-1}$ at 40° C. According to one embodiment, the ophthalmic suspension further includes an anionic polar surfactant comprising a mixture of a polysorbate non-ionic surfactant at a concentration of about 0.35 to about 0.45 weight percent and an anionic polar dimyristoylphosphatidylglycerol at a concentration of about 0.35 to about 0.55 weight percent. According to one embodiment, the ophthalmic suspension is packaged as a sterile multi-use or sterile single use container. According to one embodiment, the ophthalmic suspension is packaged in a multi-dose non-preserved (MDNP) container or a container including at least one preservative. According to one embodiment, the ophthalmic suspension increases lipid layer thickness by at least 20 nanometers at five minutes after administration. According to one embodiment, the ophthalmic suspension increases lipid layer thickness by at least 20 nanometers at 60 minutes after administration. According to one embodiment, the ophthalmic suspension increases lipid layer thickness by net of control of at least 25 nanometers at five minutes after administration. According to one embodiment, the ophthalmic suspension increases lipid layer thickness by at least 20 nanometers at four hours after administration. According to one embodiment, the ophthalmic suspension increases lipid layer thickness by net of control of at least 25 nanometers at four hours after administration.

According to another aspect, a method of increasing the lipid layer thickness is provided. The method includes the step of administering an ophthalmic suspension as provided herein to an eye of a patient in need of treatment. According to one embodiment, the lipid layer thickness is increased from baseline by at least 20 nm within five minutes of administration. According to one embodiment, the lipid layer thickness is increased from baseline by at least 20 nm at four hours after administration. According to one embodiment, the lipid layer thickness is increased from baseline by at least 25 nm at four hours after administration.

According to one aspect, a method for lubricating an eye is provided. The method includes the step of administering to the eye an ophthalmic suspension as provided herein to an eye of a patient in need of treatment. According to one embodiment, the ophthalmic suspension recreates or rebuilds one or more layers of the eye's tear film and maintains integrity of the tear film for over 60 minutes. According to one embodiment, the ophthalmic suspension recreates or rebuilds one or more layers of the eye's tear film and maintains integrity of the tear film for over 90 minutes. According to one embodiment, the ophthalmic suspension recreates or rebuilds one or more layers of the eye's tear film and maintains integrity of the tear film for over 120 minutes. According to one embodiment, the ophthalmic suspension recreates or rebuilds one or more layers of the eye's tear film and maintains integrity of the tear film for over 150 minutes.

According to one aspect, a method for alleviating symptoms of dry eye is provided. The method includes the step of administering to the eye an ophthalmic suspension as provided herein to an eye of a patient in need of treatment.

According to one aspect, a method of maintaining integrity of an eye's tear film layers which increases the eye's lipid layer thickness is provided. The method includes the step of administering an ophthalmic suspension as provided herein to an eye of a patient in need of treatment. According to one embodiment, the integrity of the tear film is maintained and lipid layer thickness is increased by at least 20 nm at 60 minutes after administration.

According to one aspect, a method of recreating or building one or more layers of an eye's tear film is provided. The method includes the step of administering an ophthalmic suspension as provided herein to an eye of a patient in need of treatment. Upon administration, the ophthalmic suspension recreates or rebuilds the one or more layers of the eye's tear film.

BRIEF DESCRIPTION OF THE FIGURES

FIG. 1 shows an enlarged view of the tear film with the different regions. The normal tear film is 3-6 microns thick. The figure shows the lipid layer, the lipid/aqueous interface, the aqueous layer, the aqueous/mucin interface, the mucin layer, and the cornea. Two of the insets show enlarged views of the lipid/aqueous interface and the aqueous/mucin interface. The third inset shows the thinning of the layers and interfaces associated with dry eye. In particular, the third inset shows the thinning of (i) the aqueous layer, (ii) the unbound mucin layer, and (iii) the bound mucin layer which is bound the surface of the corneal epithelial cells. Methodologies to evaluate tear film are further provided in U.S. Ser. No. 16/708,120 (U.S. Pub. No. 2020/0179281), the entire contents of which are incorporated herein by reference.

DETAILED DESCRIPTION OF THE DISCLOSURE

While the following terms are believed to be well understood by one of ordinary skill in the art, the following definitions are set forth to facilitate explanation of the presently disclosed subject matter.

As used herein, the terms "about" and/or "approximately" may be used in conjunction with numerical values and/or ranges. The term "about" is understood to mean those values near to a recited value. Alternatively, depending on the context, the term "about" may mean±one half a standard deviation, ± one standard deviation, or ± two standard deviations. Furthermore, the phrases "less than about [a value]" or "greater than about [a value]" should be understood in view of the definition of the term "about" provided herein. The terms "about" and "approximately" may be used interchangeably. Throughout the present specification, numerical ranges are provided for certain quantities.

As used herein, the verb "comprise" as used in this description and in the claims and its conjugations are used in its non-limiting sense to mean that items following the word are included, but items not specifically mentioned are not excluded.

As used herein, the word "comprising," or variations such as "comprises" or "comprising," will be understood to imply the inclusion of a stated element, integer or step, or group of elements, integers or steps, but not the exclusion of any other element, integer or step, or group of elements, integers or steps. The present disclosure may suitably "comprise", "consist of", or "consist essentially of", the steps, elements, and/or reagents described in the claims.

It is further noted that the claims may be drafted to exclude any optional element. As such, this statement is intended to serve as antecedent basis for use of such exclusive terminology as "solely", "only" and the like in connection with the recitation of claim elements, or the use of a "negative" limitation.

As used herein, the term "percent weight" refers to the amount based on the ophthalmic suspension, unless noted otherwise.

As used herein, the term "wax ester" refers to an ester of a fatty acid and a fatty alcohol. The wax esters provided herein may include long carbon chains. The wax esters provided herein may be present in solid particles that exhibit a melting point of from about 60° C. to about 100° C. The wax esters provided herein may be natural beeswax. Natural beeswax is also commercially available as Cera Alba or Cera Flava (White or Yellow Beeswax). The use of natural beeswax may include a hydrocarbon as a component. During the preparation of one embodiment of an ophthalmic suspension of the present disclosure, the wax esters may hydrolyze forming additional acids and/or alcohols as part of the process. The terms "wax ester dispersion" and "wax dispersion" may be used interchangeably.

As used herein, the term "particle size" refers to the size of wax ester particles alone, or in combination with, one or more oil, phospholipid, surfactant, hyaluronic acid (HA), sodium hyaluronate, or any other ophthalmic suspension component provided herein.

As used herein, the term "dwell time" refers to the time (e.g., minutes or hours) that an ophthalmic suspension remains on the eye from one application when evaluating the level or amount of lipid layer thickness from a baseline on the eye. Lipid layer thickness can be determined by interferometry instrumentation to measure dwell time on the eye.

As used herein, the term "long lasting" refers to the increase in the dwell time observed over a period of time and demonstrated compared to an untreated eye.

As used herein, the term "stable" refers to the time the tear film maintains structure between blinks.

As used herein, the term "tear film" refers to the entire protective coating provided to the eye as illustrated in FIG. 1.

As used herein, the term "dry eye" refers to a condition of the eye where the tear film is unable to perform its function of lubrication and may be caused by a lack of critical components to form a stable tear film.

As used herein, the terms "light mineral oil" and "light weight mineral oil" may be used interchangeably and refer to a low viscosity mineral oil as defined in the NF or USP formulary.

As used herein, the terms "heavy mineral oil" and "heavy weight mineral oil" may be used interchangeably and refer to a high viscosity mineral oil variant that meets the requirements of the NF or USP monographs for mineral oil.

Unless defined otherwise, all technical and scientific terms used herein have the same meanings as commonly understood by one of ordinary skill in the art to which this disclosure belongs.

The present disclosure relates to ophthalmic suspensions and related methods. The ophthalmic suspensions are particularly suited for increasing the lipid layer thickness on the eye relative to a baseline lipid layer thickness. The ophthalmic suspensions provided herein form an artificial tear film over the ocular surface of the eye and provide enhanced ocular lubrication while reducing evaporation. The ophthalmic suspensions remain on the eye and exhibit a dwell time substantially longer than any commercially available products currently on the market. The ophthalmic suspensions provided herein replicate not only the discrete layers of the tear film, but also supplement interstitial binding properties as well as build and thicken the tear film. As a result, significant improvement in the duration of dry eye relief is provided.

The ophthalmic suspensions provided include an aqueous phase and an oil phase. The aqueous phase may include water and one or more at least one wax ester, at least one anionic polar surfactant, at least one nonionic surfactant, at least one salt and at least one phosphate. The water utilized in the ophthalmic suspension vehicles provided herein may be purified or deionized water. The oil phase may include at least one mineral oil and, optionally, at least one wax ester. Thus, the at least one wax ester may be present in the aqueous phase, the oil phase, or both the aqueous phase and oil phase. According to a particular embodiment, the at least one wax ester is in either the aqueous phase or oil phase.

The ophthalmic suspensions provided herein may be formulated as an oil-in-water emulsified suspension. An emulsified suspension, as the term is used herein, is a suspension includes an aqueous and oil phase that incorporate wax ester particulate components. The wax ester particulates in the aqueous phase prefer to aggregate but are not soluble in water. The lack of solubility is attributable to the wax ester particles' significant charge stabilization. The wax ester particulates in the oil phase do not appear to aggregate or mix with water.

When an emulsified suspension is added to the eye as a standard drop, the emulsified suspension quickly differentiates permitting rapid formation of an oil film over the corneal surface without excessive oil discharge by blinking. The emulsified suspension may differentiate within about 10 blinks following application to the eye, more preferably in a time of less than about 1 minute. During and following differentiation of the emulsified suspension, the formation of the oil film is assisted by use of the surfactant combination which serves to help form the emulsified suspension and facilitate the spread of the oil over the surface of the eye as the emulsified suspension breaks.

In contrast to an emulsified ophthalmic suspension, a stable emulsion will not differentiate rapidly when applied to the ocular surface. An emulsion is typically optically opaque due to the presence of two distinct phases. Therefore, an opaque emulsion over the surface of the eye is likely to cause blurring. The duration of blur is dependent upon the time required for the emulsion to differentiate and form separate layers replicating a tear film. In addition, the emulsion is most easily added to the eye as a standard drop from an eyedropper. The eye is capable of holding a limited volume of fluid of volume that is less than 25 µL. A volume of 25 µL is substantially less than the volume of a standard drop. Therefore, if the emulsion is stable and fails to differentiate rapidly following application to the eye, excess emulsion will be discharged from the eye during blinking. Discharge of the emulsion from the eye will result in discharge of efficacious components of the treatment suspension from the eye before a long-lasting tear film can be formed. For this reason, efficacious components may not be available in sufficient quantity to form the desired tear film.

The ophthalmic suspensions as provided herein are a free flowing liquid at room temperatures such as between about 20° C. to about 30° C. The emulsified suspensions as provided herein separate into an oil phase and a water phase on contact with an eye. The surface of the eye typically exhibits a temperature of from about 32° C. to about 36° C.

According to a particular embodiment, the ophthalmic suspensions provided herein include an oil-in-water emulsion. The oil-in-water emulsion includes at least one oil and water. The water may be purified or deionized water. The oil used to form an oil-in-water emulsion may be derived from animals, plants, nuts, or other suitable sources. The oil derived from animals, plant seeds, and nuts are similar to fats and are primarily glycerides or fatty acids and consequently, contain a significant number of acid and/or ester groups rendering the oil polar. Examples of these oils are safflower oil, corn oil, canola oil, whale oil and seal oil or chemically similar oils. Additional oils that could be used to formulate an oil-in-water emulsion as provided herein include a vegetable oil such as a castor oil, almond oil, myrcia oil, corn oil, peanut oil, canola oil, safflower oil, kola nut oil, light olive oil, bay leaf oil, or other generally recognized as safe (GRAS) oils listed as being appropriate for ocular formulation. Alternatively, the oil may be an oil suited for forming liposomes. According to one embodiment, the oil is a linear hydrocarbon oil having from 10 to 150 carbon atoms and, more preferably, the oil is a saturated n-alkane or isoalkane hydrocarbon having from 10 to 26 carbon atoms. Unsaturated alkene hydrocarbons may be used but are less chemically stable.

According to one embodiment, the oil as provided herein is a mineral oil. According to one embodiment, the oil as provided herein is a lightweight mineral oil. According to one embodiment, the oil as provided herein is a heavy weight mineral oil.

According to one embodiment, the oil includes a mixture of light weight mineral oil and heavy weight mineral oil each having differing viscosities. According to a particular embodiment, the light weight mineral oil exhibits a kinetic viscosity of from about 3.0 mm$^2$s$^{-1}$ to about 34.4 mm$^2$s$^{-1}$ at 40° C. According to a particular embodiment, the heavy weight mineral oil exhibits a viscosity of kinetic viscosity of from about 34.5 mm$^2$s$^{-1}$ to about 150 mm$^2$s$^{-1}$ at 40° C. According to yet another embodiment, the light weight mineral oil exhibits a kinetic viscosity of from about 28 mm$^2$s$^{-1}$ to about 30 mm$^2$s$^{-1}$ at 40° C. According to yet another embodiment, the heavy weight mineral oil exhibits a viscosity of kinetic viscosity of from about 65 mm$^2$s$^{-1}$ to about 71 mm$^2$s$^{-1}$ at 40° C.

The amount of oil within the oil-in-water emulsion may vary within reasonable limits such that application to the eye does not exceed 25 µL. According to one embodiment, the volume does not exceed 15 µL. According to one embodiment, the volume varies between about 1 µL and 10 µL. According to one embodiment, the volume varies between about 1 µL and 30 µL.

The total amount of oil or combination of oils may be present in the ophthalmic suspensions in an amount of at least about 0.1 percent by weight based on the total weight of the ophthalmic suspension. According to one embodiment, the oil or combination of oils is present in an amount of at least about 0.5 percent by weight. According to one embodiment, the oil or combination of oils is present in an amount of at least about 1.0 percent by weight. According to one embodiment, the oil or combination of oils is present in an amount of at least about 1.5 percent by weight. According to one embodiment, the oil or combination of oils is present in an amount of less than about 12.5 percent by weight. According to one embodiment, the oil or combination of oils is present in an amount of less than about 10.0 percent by weight. According to one embodiment, the oil or combination of oils is present in an amount of less than about 7.5 percent by weight. According to one embodiment, the oil or combination of oils is present in an amount of less than about 6.6 percent by weight. According to one embodiment, the oil or combination of oils is present in an amount of less than about 6.5 percent by weight. According to one embodiment, the oil or combination of oils is present in an amount of between about 0.5 percent by weight and about 12.5 percent by weight. According to one embodiment, the oil or combination of oils is present in an amount of between about 1.0 percent by weight and about 8.5 percent by weight. According to one embodiment, the oil or combination of oils is present in an amount of between about 3.5 percent by weight and about 7.5 percent by weight. According to one embodiment, the oil or combination of oils is present in an amount of between about 4.0 percent by weight and about 7.0 percent by weight. According to one embodiment, the oil or combination of oils is present in an amount of between about 4.4 percent by weight and about 6.6 percent by weight. According to one embodiment, the oil or combination of oils is present in an amount of between about 4.95 percent by weight and about 6.05 percent by weight.

According to one embodiment, the oil includes a mixture of two or more oils of differing weight. According to such an embodiment, the oil is a mixture of at least one light weight oil and at least one heavy weight oil. According to a particular embodiment, the oil is a mixture of the mineral oils marketed under the tradenames Drakeol® 15 (light weight mineral oil) and Drakeol® 35 (white, heavy mineral oil). According to one embodiment, the lightweight mineral oil may be present in an amount of from about 0.5 percent by weight to about 1.5 percent by weight. According to one embodiment, the lightweight mineral oil may be present in an amount of from about 0.6 percent by weight to about 1.4 percent by weight. According to one embodiment, the lightweight mineral oil may be present in an amount of from about 0.7 percent by weight to about 1.3 percent by weight. According to one embodiment, the lightweight mineral oil may be present in an amount of from about 0.8 percent by weight to about 1.2 percent by weight.

According to one embodiment, the heavy weight mineral oil may be present in an amount of from about 2.7 percent by weight to about 6.5 percent by weight. According to one embodiment, the heavy weight mineral oil may be present in an amount of from about 2.9 percent by weight to about 6.3 percent by weight. According to one embodiment, the heavy weight mineral oil may be present in an amount of from about 3.1 percent by weight to about 6.1 percent by weight. According to one embodiment, the heavy weight mineral oil may be present in an amount of from about 3.3 percent by weight to about 5.9 percent by weight. According to one embodiment, the heavy weight mineral oil may be present in an amount of from about 3.5 percent by weight to about 5.7 percent by weight. According to one embodiment, the heavy weight mineral oil may be present in an amount of from about 3.7 percent by weight to about 5.5 percent by weight. According to one embodiment, the heavy weight mineral oil may be present in an amount of from about 4.05 percent by weight to about 4.95 percent by weight.

According to one embodiment, the light weight mineral oil may be present in an amount of about 1.0 percent by weight and the heavy weight mineral oil may be present in an amount of about 4.5 percent by weight.

The ophthalmic suspensions provided herein include a wax ester dispersion. The wax dispersion includes at least one wax ester. While not being bound to a particular theory, the role of wax esters and their hydrolysis products is believed to maintain the integrity of the interstitial layers themselves, binding the mucin layer to the aqueous layer and aqueous layer to the lipid layer. In addition, the wax esters serve to build up an thicken the mucin, the aqueous layer, and the lipid layer themselves. The binding process and subsequent homeostasis enabled by the wax esters allows the layers of the tear film to cling to each other, thus allowing the entire tear film to remain on the eye for extended periods of time. The ophthalmic suspensions provided herein penetrate all layers of the tear film including the five interstitial layers of which no product has incorporated previously.

According to one embodiment, the at least one wax ester is present in an amount of at least about 0.2 weight percent. According to one embodiment, the at least one wax ester is present in an amount of at least about 0.3 weight percent. According to one embodiment, the at least one wax ester is present in an amount of at least about 0.4 weight percent. According to one embodiment, the at least one wax ester is present in an amount of at least about 0.5 weight percent. According to one embodiment, the at least one wax ester is present in an amount of at least about 0.6 weight percent. According to one embodiment, the at least one wax ester is present in an amount of at least about 0.7 weight percent. According to one embodiment, the at least one wax ester is present in an amount of at least about 0.8 weight percent. According to one embodiment, the at least one wax ester is present in an amount of at least about 0.9 weight percent. According to one embodiment, the at least one wax ester is present in an amount of at least about 1.0 weight percent. According to one embodiment, the at least one wax ester is present in an amount of less than about 1.8 weight percent. According to one embodiment, the at least one wax ester is present in an amount of from about 0.2 weight percent to about 1.8 weight percent. According to one embodiment, the at least one wax ester is present in an amount of from about 0.4 weight percent to about 1.6 weight percent. According to one embodiment, the at least one wax ester is present in an amount of from about 0.6 weight percent to about 1.4 weight percent. According to one embodiment, the at least one wax ester is present in an amount of from about 0.8 weight percent to about 1.2 weight percent. According to one embodiment, the at least one wax ester is present in an amount of about 1.0 weight percent.

According to one embodiment, the at least one wax ester is a beeswax. According to one embodiment, the beeswax is a natural beeswax. The beeswax may be Cera Alba, Cera Flava, or a combination thereof. The beeswax may be USDA Certified Organic beeswax or conventional natural beeswax. According to one embodiment, at least one wax ester is a synthetic beeswax.

According to one embodiment, the wax ester particles may be emulsified into the ophthalmic suspensions to form a range of specific particle sizes. The irregular shape and charge of the particles themselves allow the wax ester particles more surface area to interact with the oil as provided herein and allows the wax ester particles to break down at a varied rate, with the smaller wax ester particles and oil particles breaking down quickly, and the larger wax ester particles breaking down more slowly. As wax ester particles are broken down, the oil and wax esters particles are believed to interact with the natural tear film to support a more stable barrier for the evaporation-prone aqueous tear film.

The ophthalmic suspensions provided herein include wax ester particles that exhibit a particle size with allow wax ester particles to be retained on the eye. According to one embodiment, the wax ester particles exhibit a mean particle size of at least about 2.0 microns. According to one embodiment, the wax ester particles exhibit a mean particle size of at least about 3.0 microns. According to one embodiment, the wax ester particles exhibit a mean particle size of at least about 4.0 microns. According to one embodiment, the wax ester particles exhibit a mean particle size of at least about 5.0 microns. According to one embodiment, the wax ester particles exhibit a mean particle size of less than about 30.0 microns. According to one embodiment, the wax ester particles exhibit a mean particle size of less than about 25.0 microns. According to one embodiment, the wax ester particles exhibit a mean particle size of less than about 24.0 microns. According to one embodiment, the wax ester particles exhibit a mean particle size of less than about 23.0 microns. According to one embodiment, the wax ester particles exhibit a mean particle size of less than about 22.0 microns. According to one embodiment, the wax ester particles exhibit a mean particle size of less than about 21.0 microns. According to one embodiment, the wax ester particles exhibit a mean particle size of less than about 20.0 microns. According to one embodiment, the wax ester particles exhibit a mean particle size of at least about 2.0 microns but less than about 25.0 microns. According to one embodiment, the wax ester particles exhibit a mean particle size of at least about 2.0 microns but less than about 20.0 microns. According to one embodiment, the wax ester particles exhibit a mean particle size of at least about 2.0 microns but less than about 15.0 microns. According to one embodiment, the wax ester particles exhibit a mean particle size of at least about 3.0 microns but less than about 24.0 microns. According to one embodiment, the wax ester particles exhibit a mean particle size of at least about 4.0 microns but less than about 23.0 microns. According to one embodiment, the wax ester particles exhibit a mean particle size of at least about 5.0 microns but less than about 22.0 microns. According to one embodiment, the wax ester particles exhibit a mean particle size of at least about 6.0 microns but less than about 21.0 microns. According to one embodiment, the wax ester particles exhibit a mean particle size of at least about 7.0 microns but less than about 20.0 microns.

The wax ester dispersion includes at least one surfactant. According to one embodiment, the wax dispersion includes two or more surfactants. According to one embodiment, the wax dispersion includes a combination of surfactants for the dual purpose of stabilizing the suspension as well as spreading and maintaining the suspension over the ocular surface following application to the eye. The surfactant combination may include a primary surfactant and secondary surfactant. The at least one surfactant enables formation of a suspension that is stable in manufacture and during storage, but desirably meta stable when applied to the ocular surface. The at least one surfactant as provided herein is suitable for rapidly differentiation when applied to the eye whereby a non-blurring film of oil is rapidly formed over the ocular surface and disseminates the wax ester through each phase of the emulsified suspension.

According to one embodiment, the at least one surfactant includes at least one polyoxyethylene sorbitan monooleate such as polyoxyethylene-sorbitan-20 mono-oleate which is commercially available as Polysorbate 80 or Tween 80. According to one embodiment, the polyoxyethylene sorbitan monooleate may be present in the ophthalmic suspension in an amount of from about 0.1 percent weight to about 0.7 percent weight. According to one embodiment, the polyoxyethylene sorbitan monooleate may be present in the ophthalmic suspension in an amount of from about 0.2 percent weight to about 0.6 percent weight. According to one embodiment, the polyoxyethylene sorbitan monooleate may be present in the ophthalmic suspension in an amount of from about 0.3 percent weight to about 0.6 percent weight. According to one embodiment, the polyoxyethylene sorbitan monooleate may be present in the ophthalmic suspension in an amount of from about 0.4 percent weight to about 0.6 percent weight.

According to one embodiment, the at least one surfactant includes diphosphatidylglycerol such as dimyristoylphosphatidylglycerol or 1,2-Dimyristoyl-sn-glycero-3-phosphorylglycerol sodium salt (DMPG) which is commercially available. The surfactant may be a lysophosphatidylcholine, a phosphatidic acid, a phosphatidylcholine, a phosphatidylethanolamine, a phosphatidylglycerol, or a phosphatidylserine. In other embodiments, the surfactant includes at least one anionic surfactant. According to one embodiment, the anionic surfactant may be one or more of an anionic polar phospholipid, such as a lysophosphatidylcholine, a phosphatidic acid, a phosphatidylcholine, a phosphatidylethanolamine, a phosphatidylglycerol, or a phosphatidylserine. According to another embodiment, the anionic polar phospholipid may be one or more of phosphatidic acid (PA), phosphatidylserine (PS), phosphatidylinositol (PI), and its phosphorylated derivatives the phosphoinositides (e.g. phosphatidylinositol-4-phosphate [PI4P] and phosphatidylinositol-4,5-bisphosphate, also dimyristoylphopatidyl glycerol. According to one embodiment, the anionic surfactant is a dimyristoylphosphatidylglycerol. According to one embodiment, the surfactant is a mixture of two surfactants as provided herein. According to one embodiment, the surfactant is a combination of two anionic polar phospholipids.

According to one embodiment, the anionic polar surfactant is a mixture of a Tween 80 and anionic polar dimyristoylphosphatidylglycerol.

According to one embodiment, the dimyristoylphosphatidylglycerol may be present in the ophthalmic suspension in an amount of from about 0.1 percent weight to about 0.7 percent weight. According to one embodiment, the dimyristoylphosphatidylglycerol may be present in the ophthalmic suspension in an amount of from about 0.2 percent weight to about 0.6 percent weight. According to one embodiment, the dimyristoylphosphatidylglycerol may be present in the ophthalmic suspension in an amount of from about 0.3 percent weight to about 0.6 percent weight. According to one embodiment, the dimyristoylphosphatidylglycerol may be present in the ophthalmic suspension in an amount of from about 0.4 percent weight to about 0.6 percent weight.

According to one embodiment, the ophthalmic suspensions provided herein include one or more phosphates. According to one embodiment, the ophthalmic suspensions include both a monobasic and a dibasic phosphate.

According to a particular embodiment, the monobasic phosphate is monosodium phosphate (monobasic sodium phosphate) such as $NaH_2PO_4$. According to one embodiment, the monobasic phosphate may be present in an amount of from about 0.01 percent by weight to about 0.05 percent by weight. According to one embodiment, the monobasic phosphate may be present in an amount of from about 0.02 percent by weight to about 0.04 percent by weight. According to one embodiment, the monobasic phosphate may be present in an amount of about 0.03 percent by weight.

According to a particular embodiment, the dibasic phosphate is disodium phosphate (sodium hydrogen phosphate or sodium phosphate dibasic) such as $Na_2HPO_4$. According to one embodiment, the dibasic phosphate may be present in an amount of from about 0.1 percent by weight to about 0.5 percent by weight. According to one embodiment, the dibasic phosphate may be present in an amount of from about 0.2 percent by weight to about 0.3 percent by weight. According to one embodiment, the dibasic phosphate may be present in an amount of about 0.25 percent by weight.

According to one embodiment, the ophthalmic suspensions provided herein include at least one salt. According to one embodiment, the at least one salt is sodium chloride or other suitable salt for ophthalmic application. The at least one salt may be present in an amount of from about 0.50 percent weight to about 0.75 percent weight. According to another embodiment, the at least one salt may be present in an amount of from about 0.55 percent weight to about 0.70 percent weight. According to another embodiment, the at least one salt may be present in an amount of about 0.55 percent weight. According to another embodiment, the at least one salt may be present in an amount of about 0.67 percent weight.

According to one embodiment, the ophthalmic suspensions provided herein include at least one glycosylaminoglycan. A suitable glycosylaminoglycan includes hyaluronic acid (HA), the corresponding sodium salt, sodium hyaluronate, or a combination thereof. According to one embodiment, the hyaluronic acid or sodium hyaluronate may be present in the ophthalmic suspensions in an amount of from about 0.06 percent about to about 0.5 percent weight. According to one embodiment, the hyaluronic acid or sodium hyaluronate may be present in the ophthalmic suspensions in an amount of from about 0.07 percent about to about 0.4 percent weight. According to one embodiment, the hyaluronic acid or sodium hyaluronate may be present in the ophthalmic suspensions in an amount of from about 0.08 percent about to about 0.3 percent weight. According to one embodiment, the hyaluronic acid or sodium hyaluronate may be present in the ophthalmic suspensions in an amount of from about 0.09 percent about to about 0.2 percent weight. According to one embodiment, the hyaluronic acid or sodium hyaluronate may be present in the ophthalmic suspensions in an amount of about 0.1 percent weight.

According to one embodiment, the ophthalmic suspensions provided herein optionally include ethylenediaminetetraacetic acid (EDTA). According to one embodiment, the EDTA may be present in the ophthalmic suspension in an amount of from about 0.007 percent weight to about 0.02 percent weight. According to one embodiment, the EDTA may be present in the ophthalmic suspension in an amount of from about 0.008 percent weight to about 0.015 percent weight. According to one embodiment, the EDTA may be present in the ophthalmic suspension in an amount of about 0.01 percent weight.

According to one embodiment, the ophthalmic suspensions provided herein optionally include at least one anti-inflammatory compound such as deactivated brewer's yeast or adenosine diphosphate ribose. When present, the at least one anti-inflammatory compound does not impact ophthalmic suspension stability or on-eye performance. According to one embodiment, the anti-inflammatory compound may be present in the ophthalmic suspension in an amount of from about 0.02 percent weight to about 1.0 percent weight.

Other additives may be present in the ophthalmic suspension. Such additives include minor amounts of neutral lipids and oils such as one or more triglycerides, partially hydroylyzed esters, cholesterol esters, high molecular weight isoprenoids; stabilizers, additional surfactants; mucomimetics (e.g., HP Guar); preservatives; pH adjusters; salt, buffer, glycerol, a sugar in sufficient concentration to form a mildly hypotonic composition such that the emulsion is not stable in the ocular environment; emollients; demulcents; polymers of ethylene oxide, propylene oxide, or butylene oxide; carboxymethylcellulose (CMC); hydroxypropyl methylcellulose (HPMC); polyacrylic acid (PAA); polyethylene glycol; (PEG) propylene glycol (PG); or polyvinyl alcohol (PVA).

The ophthalmic suspensions provided herein have an osmolality that can be adjusted by the concentration of salts such as NaCl. According to one embodiment, the ophthalmic suspensions provided herein have an osmolality of at least about 245 mOsmol/kg. According to one embodiment, the ophthalmic suspensions provided herein have an osmolality of at least about 260 mOsmol/kg. According to one embodiment, the ophthalmic suspensions provided herein have an osmolality of from about 245 mOsmol/kg to about 315 mOsmol/kg. According to one embodiment, the ophthalmic suspensions provided herein have an osmolality of from about 245 mOsmol/kg to about 310 mOsmol/kg. According to one embodiment, the ophthalmic suspensions provided herein have an osmolality of from about 255 mOsmol/kg to about 305 mOsmol/kg. According to one embodiment, the ophthalmic suspensions provided herein have an osmolality of from about 270 mOsmol/kg to about 300 mOsmol/kg. According to one embodiment, the ophthalmic suspensions provided herein have an osmolality of from about 275 mOsmol/kg to about 295 mOsmol/kg. According to one embodiment, the ophthalmic suspensions provided herein have an osmolality of from about 280 mOsmol/kg to about 290 mOsmol/kg. According to one embodiment, the ophthalmic suspensions provided herein have an osmolality of from about 282 mOsmol/kg to about 289 mOsmol/kg. According to one embodiment, the ophthalmic suspensions provided herein have an osmolality of from about 285 mOsmol/kg to about 287 mOsmol/kg. According to one embodiment, the ophthalmic suspensions provided herein have an osmolality of about 286 mOsmol/kg.

According to one embodiment, the ophthalmic suspensions provided herein have a pH of between about 6.8 and 7.8. According to one embodiment, the ophthalmic suspensions provided herein have a pH of between about 6.9 and 7.7. According to one embodiment, the ophthalmic suspensions provided herein have a pH of between about 7.0 and 7.6. According to one embodiment, the ophthalmic suspensions provided herein have a pH of between about 7.0 and 7.4. According to one embodiment, the ophthalmic suspensions provided herein have a pH of between about 7.1 and 7.5. According to one embodiment, the ophthalmic suspensions provided herein have a pH of between about 7.2 and 7.4. According to one embodiment, the ophthalmic suspensions provided herein have a pH of about 7.2. According to one embodiment, the ophthalmic suspensions provided herein have a pH of about 7.3. The pH may be adjusted by addition of pH adjusters such as HCl or citric acid or a base such as NaOH.

The viscosity of the ophthalmic suspensions described herein may vary but will exhibit a viscosity allows appropriate drop size for application to the eye. According to one embodiment, the viscosity of the ophthalmic suspensions provided herein exhibit a viscosity of from about 5 centipoise at 25° C. to about 8 centipoise at 25° C. The viscosity of the ophthalmic suspensions described herein may be measured using techniques well-known to those skilled in the art. Non-limiting examples of methods to measure viscosity include falling ball viscometers, viscosity cups, consistometers (measuring flow on an incline), capillary glass viscometers, or rotational viscometers. A variety of instruments are commercially available (Cole-Palmer Instrument Co., Vernon Hills, Ill., USA).

The ophthalmic suspensions provided herein are preservative-free. In some embodiments, preservative-free ophthalmic suspensions are delivered in single use packages because of the risk of bacterial contamination associated with conventional multi-use applications. In another embodiment, the ophthalmic suspension is delivered in a sterile multidose bottle. Examples include the Aptar Pharma (Crystal Lake, Ill., USA) multidose squeeze dispenser which operates mechanically and utilizes a filter membrane (see PCT Publication Nos. WO 2017/074420 and WO 2017/132190 (Aptargroup, Inc.); Nemera La Verpillier (France) multidose squeeze bottle (see PCT Publication WO2013/140069)).

According to an alternative embodiment, the ophthalmic suspensions provided herein may include at least one preservative. According to an alternative embodiment, the ophthalmic suspensions provided herein may include at least one borate buffer.

Methods of preparing ophthalmic suspension vehicles are provided. According to one embodiment, the method of preparation of the ophthalmic suspension vehicle includes the step of separately preparing a mixture of the oils (e.g., heavy weight mineral oil and light weight mineral oil) and adding the wax ester component, such as beeswax, and heating the mixture to a temperature above the melting point of the wax ester (e.g., from about 63° C. to about 71° C.). In a separate water/aqueous phase, the salts, phosphates, surfactants and any other water-soluble ingredient may be prepared and heated to approximately 85° C. The oil phase may then be slowly added to the water/aqueous phase, mixed, and homogenized to form the ophthalmic suspension vehicle. The resulting ophthalmic suspension vehicle is autoclaved. Throughout the process, the ophthalmic suspension vehicle continues to be mixed.

According to one embodiment, the method of preparation of the ophthalmic suspension vehicle includes the step of separately preparing the oil phase (e.g., heavy weight mineral oil and light weight mineral oil) heating to a temperature of from about 63° C. to about 71° C. The step of preparing the oil phase may optionally include the step of adding or introducing at least one wax ester to the oil phase followed by heating the mixture to a temperature above the melting point of the wax ester (e.g., from about 63° C. to about 71° C.).

According to one embodiment, the method of preparation of the ophthalmic suspension vehicle includes the step of separately preparing the aqueous phase. The aqueous phase may be prepared by mixing the at least one wax ester, at least one salt, at least one phosphate, at least one surfactant and any other water-soluble ingredient followed by heating the mixture to a temperature above the melting point of the wax ester (e.g., from about 63° C. to about 71° C.).

According to one embodiment, the oil phase as provided herein may then slowly added to the aqueous phase, mixed, and homogenized to form the ophthalmic suspension vehicle. The resulting ophthalmic suspension vehicle may then be autoclaved. Thus, according to such an embodiment, the individual oil phase and aqueous phase are not separately autoclaved prior to being combined. According to one embodiment, the resulting ophthalmic suspension vehicle is not autoclaved and sterilized according to an alternative method such as, for example, e-beam or gamma irradiation, or filtration.

According to an alternative embodiment, a method of preparing an ophthalmic suspension vehicle is provided. This alternative method includes the step of preparing a wax dispersion by mixing or dissolving at least one wax ester (such as a natural beeswax) with a surfactant and purified or deionized water. According to one embodiment, the at least one wax ester may be mixed or dissolved in such a way that the natural wax esters can be delivered in a controlled manner leading to increased dwell time on the eye. According to one embodiment, the step of preparing a wax dispersion includes dissolving one or more salts and one or more phosphates such as a monosodium phosphate and disodium phosphate in the purified or deionized water. According to one embodiment, the step of preparing a wax dispersion includes heating the one or more salts, phosphates, surfactants and wax esters and stirring the resulting dispersion. According to one embodiment, the dispersion is heated to about 70° C. to about 90° C. According to a particular embodiment, wax particle dispersions may be prepared by homogenization of melted beeswax (~1.0%) in purified or distilled water containing salts, phosphates with added Octoxynol-40 (~0.2% 1,2-Dimyristoyl-sn-glycero-3-phosphorylglycerol sodium salt (DMPG)) at about 75° C. The high cloud point of Octoxynol-40 (>100° C.) allows emulsifying efficiency at higher temperatures by a decrease in its water solubility (effective lowering of the HLB value).

The alternative method includes the step of preparing an oil-in-water emulsion. According to one embodiment, the step of preparing an oil-in-water emulsion includes mixing differing weight or viscosity of mineral oils as described herein and heating the mixture of mineral oils to a temperature of from about 65° C. to about 75° C. According to one embodiment, the step of preparing an oil-in-water emulsion includes dropwise introducing the mixture of heated mineral oils to purified or deionized water and homogenizing the water and mineral oil mixture to form an oil-in-water emulsion. The pH of the oil-in-water emulsion may be adjusted to a range of from about 6.8 to about 7.8.

The alternative method includes the step of separately autoclaving the wax dispersion and the oil-in-water emulsion. The integrity of the emulsion is maintained during autoclaving.

While not being bound to a particular theory, the mechanism involved in the irreversible aggregation of the wax (wax breakout) under autoclave conditions is believed to involve the presence of relatively high (approximately isotonic) salt concentrations. This high ionic loading is believed to significantly decrease the zeta-potential of the wax ester particles, which removes an important stabilization mechanism when these dispersions are subjected to autoclave conditions.

The alternative method includes the step of aseptically blending the autoclaved beeswax dispersion and the oil-in-water emulsion so as to prepare the ophthalmic suspension vehicles as provided herein. According to one embodiment, the wax ester particles may be stabilized by the surfactant in the oil phase preventing flocculation and droplet aggregations during cooling.

To maintain a shelf stable suspension, separate preparation and autoclaving of the wax ester particle dispersion and emulsion components is performed, followed by an aseptic blending step to ensure product sterility. The aseptic blending step of the autoclaved beeswax dispersion and the oil-in-water emulsion ensures that the desired final concentrations of mineral oil, beeswax, and other components are present in the ophthalmic suspension. According to one embodiment, the oil-in-water emulsion is formulated with increased component levels, while the beeswax particles are emulsified in water with an added surfactant. The concentrations of the various components in the two fractions (before autoclaving) can be tailored to permit a relatively wide variation of final emulsified suspension compositions.

According to one embodiment, the method of preparation includes the step of separately preparing a mixture of the oils (e.g., heavy weight mineral oil and light weight mineral oil) and adding the wax ester component such as beeswax and heating the mixture to a temperature above the melting point of the wax ester (e.g., 63° C. to 71° C.). In a separate phase, the salts, phosphates, surfactants and any other water-soluble ingredient are prepared and heated to approximately 85° C. The oil phase is slowly added to the water phase, mixed, and homogenized. The resulting preparation is autoclaved. Throughout the process, the preparation continues to be mixed.

According to one embodiment, the method of preparation includes the step of mixing an oil phase containing light mineral, mineral oil and wax ester (e.g., natural or synthetic bees wax) with an aqueous phase containing a salt, phosphate, surfactant and a water soluble glycosaminoglycan followed by homogenizing and autoclaving to form a complex combination of particles. Larger particles are observed in the resulting preparation that are about 2 microns to about 15 microns according to particle analysis via Microtrac particle size analysis. According to one embodiment, measurement of particles for zeta potential or surface charge demonstrate zeta potential of greater than −60 mV. According to one embodiment, measurement of particles for zeta potential or surface charge demonstrates zeta potential of from about −60 mV to about −110 mV. Within the preparation, there are both charged particles resulting from interaction with the surfactant that may found in the water phase and particles found in the oil phase which are submicron in size. The particles in the oil phase may be wax-ester particles, or oil wax-ester mixtures that may either have neutral charge or surface charge.

Large sized particle dispersions cannot be prepared in the absence of added surfactant. The operating particle formation mechanism is different from a simple nucleation and particle growth model used in the formation of submicron sized dispersions. The added surfactant stabilizes the growing beeswax droplets during homogenization. The surfactant prevents droplet aggregation during the cooling period after autoclaving. The chemistry of the system yields particle dispersions that are stable in the autoclave (as melted wax droplets), but which aggregate irreversibly once the decreasing sample temperature during sample cooling approaches the melting point (crystallization temperature) of the beeswax. Specifically, the presence of surfactant such as DMPG is also believed to aid in stabilizing the beeswax emulsions at the high temperatures present in the autoclave. Particularly, the surfactant is believed to stabilize the melted wax droplets by re-partitioning from the dissolved state in the aqueous phase onto the particle/droplet surfaces and preventing flocculation. As temperature continuously increases during the autoclaving process, the surfactant becomes increasingly insoluble in water, and tends to migrate towards the particle surface (droplet/aqueous interface) helping to stabilize the melted wax droplet.

Although the zeta potential values cannot be measured under autoclave conditions, sealed beeswax particles/droplets dispersions remain stable at 121° C. (with gentle stirring) when dispersed in water. Further, the oil-in-water emulsions provided herein are not subjected to significant amounts of particle aggregation when prepared according to the present methods. Strong long-term stability characteristics are believed to be the result of such methods.

EXAMPLES

Ophthalmic Suspension Preparation

The ophthalmic suspension utilized in the Examples provided herein is set forth in Table 1, below.

TABLE 1

| Component | Weight % |
| --- | --- |
| Water | 90.00-95.00 |
| NaCl | 0.10-0.90 |
| NaH$_2$PO$_4$ | 0.01-0.05 |
| Na$_2$HPO$_4$ | 0.10-0.50 |
| Tween-80 | 0.10-0.70 |
| DMPG | 0.35-0.55 |
| Wax ester | 0.80-1.20 |
| Sodium Hyaluronate | 0.06-0.50 |
| Drakeol ®-35 | 2.7-6.5 |
| Drakeol ®-15 | 0.50-1.50 |

To prepare a 500 gram batch of the ophthalmic suspension, NaCl, dimyristoylphosphatidylglycerol (DPMG), NaH$_2$PO$_4$ and Na$_2$HPO$_4$ were dissolved in purified water in a beaker. Tween 80, DPMG, and sodium hyaluronate were added to the aqueous solution and heated with continuous stirring to 85° C. (+/−2° C.). In a separate glass beaker, Drakeol® 15, Drakeol® 35 and wax ester were mixed and heated to 71° C. (+/−2° C.) with continuous stirring for 10 minutes (+/−20 seconds). The aqueous phase was homogenized for 30 seconds (+/−5 seconds). The oil phase was pre-heated to 71° C. (+/−2° C.) and added dropwise to the aqueous phase at 85° C. (+/−2° C.), while the homogenizer was running. After the addition of the oil was complete, the homogenizer was run. The target homogenization speed was around 10,000 RPM (+/−400 RPM) and the target homogenization time was about 4 min (+/−20 seconds). The homogenization procedure was terminated and stirring continued until the suspension reached room temperature (approximately 4 hours). While stirring, the pH and osmolality were checked and adjusted (target pH: 7.2-7.4: osmolality of 240 mOsmol/kg-290 mOsmol/kg). While stirring, the suspension mixture was dispensed using a syringe to an autoclavable bottle and charged with a magnetic stir bar. The bottle and autoclave were closed for 35 minutes (+/−1 minute) and heated to/at 121° C. and 15 psi while stirring. The suspension was allowed to cool to room temperature while stirring (approximately 6 hours).

Example 1

Wax Ester Impact on Ocular Emulsion Retention

Testing was conducted to determine wax ester impact on lipid layer thickness. At instillation of a single drop, blurring and comfort scores were noted and interferometric measurements of lipid layer thickness were then taken from both eyes at 5, 30, 60, and 120-minute intervals. The improvement of lipid layer thickness over baseline was calculated and subtracted (or added) the net result of the control drop at each time interval. The results for the ophthalmic solution of Table 1 is illustrated in Table 2. Ophthalmic solutions that contain no wax ester (commercially available as Soothe® XP) and two additional commercially available solutions—Refresh Optive® Advanced and Systane® Balance—were tested with results shown in Table 2, 3, 4 and 5, respectively, below.

TABLE 2

Ophthalmic Suspension

| Time Interval | Increase in LLT Over Baseline Relative to Control (nm) |
|---|---|
| 5 Minutes | 29 |
| 30 Minutes | 31 |
| 60 Minutes | 29 |
| 120 Minutes | 25 |

TABLE 3

Refresh Optive ® Advanced

| Time Interval | Increase in LLT Over Baseline Relative to Control (nm) |
|---|---|
| 5 Minutes | 2 |
| 30 Minutes | 7 |
| 60 Minutes | −2 |
| 120 Minutes | 1 |

TABLE 4

Soothe ® XP (no wax)

| Time Interval | Increase in LLT Over Baseline Relative to Control (nm) |
|---|---|
| 5 Minutes | 13 |
| 30 Minutes | 1 |
| 60 Minutes | −2 |
| 120 Minutes | −4 |

TABLE 5

Systane ® Balance

| Time Interval | Increase in LLT Over Baseline Relative to Control (nm) |
|---|---|
| 5 Minutes | 2 |
| 30 Minutes | 4 |
| 60 Minutes | 8 |
| 120 Minutes | 1 |

Testing determined that mineral oil alone added to the ocular environment is rapidly lost, most likely through the regular exchange of the tear film or by ocular drainage from the tear glands. The addition of the wax ester was shown to provide an ophthalmic suspension that is retained for an extended period in the ocular environment allowing the ophthalmic suspension to continue to augment an increase the lipid layer.

Example 2

Wax and Surfactant Selection

The inclusion of different wax esters provides an indication of the key attributes required to maintain the effects of the addition of wax esters to the ocular environment. In order to understand the role demonstrating enhanced enhancement of the lipid layer, the role of the wax ester ingredient and the use of surfactant ingredients was evaluated. The following wax esters were evaluated: Wax ester, Kester K-24, Branched Kester BK-40, and Synthetic Wax ester.

One or more of the following surfactants were utilized with the noted wax esters: DMPG DimyristoylphosphatidylGlycerol (an anionic phospholipid); IGEPAL CA 897 Ethoxylated(40)-1,1,3,3 Tetramethylbutyl phenol; Phospholipon 90G phosphatidylcholine (zwitterionic charged phospholipid); and IGEPAL CO-890 Polyoxyethylene (40) nonylphenyl ether, branched. The results are summarized in Tables 6-10, below.

TABLE 6

Beeswax

| Time Interval | Increase in LLT Over Baseline Relative to Control (nm) | | | |
|---|---|---|---|---|
| | 90G | CA897 | CO-890 | DMPG |
| 5 Minutes | 14 | 20 | 7 | 29 |
| 30 Minutes | 20 | 24 | 24 | 31 |
| 60 Minutes | 17 | 19 | 23 | 29 |
| 120 Minutes | 15 | 18 | 16 | 25 |

TABLE 7

BK Kester

| Time Interval | Increase in LLT Over Baseline Relative to Control (nm) | | |
|---|---|---|---|
| | 90G | CA897 | DMPG |
| 5 Minutes | 10 | 3 | 0 |
| 30 Minutes | 4 | 1 | 6 |
| 60 Minutes | −1 | 0 | 7 |
| 120 Minutes | n/a | 5 | 14 |

TABLE 8

BK Kester/Kester K24

| Time Interval | Increase in LLT Over Baseline Relative to Control (nm) | | |
|---|---|---|---|
| | 90G | CA897 | DMPG |
| 5 Minutes | 5 | 3 | −24 |
| 30 Minutes | −11 | 24 | 2 |
| 60 Minutes | −17 | 4 | −2 |
| 120 Minutes | n/a | n/a | n/a |

TABLE 9

Kester K24

| Time Interval | Increase in LLT Over Baseline Relative to Control (nm) | | |
|---|---|---|---|
| | 90G | CA897 | DMPG |
| 5 Minutes | 2 | 1 | 4 |
| 30 Minutes | 28 | 1 | 2 |
| 60 Minutes | 5 | −4 | 3 |
| 120 Minutes | −1 | n/a | n/a |

TABLE 10

Synthetic Beeswax

| Time Interval | Increase in LLT Over Baseline Relative to Control (nm) | | |
|---|---|---|---|
| | 90G | CA897 | DMPG |
| 5 Minutes | 20 | 24 | 22 |
| 30 Minutes | 27 | 26 | 20 |
| 60 Minutes | 20 | 18 | 10 |
| 120 Minutes | 13 | 11 | 8 |

The preceding results illustrate that lower melting point wax esters had no significant on-eye effect relative to the control product and were similar to the commercially available product. The natural beeswax wax ester and the synthetic beeswax wax ester saw improved results with all surfactant combinations with the natural beeswax wax ester demonstrating the best results overall.

Example 3

Wax and Surfactant Combination Selection

Natural and synthetic beeswax wax esters were tested to identify which surfactant allowed for quick lipid layer improvement and extended residence time on the eye (in addition to in-bottle stability). One or more of the following surfactants were utilized with the noted wax esters: DMPG dimyristoylphosphatidylglycerol (an anionic phospholipid); IGAPEL CA 897 Ethoxylated(40)-1,1,3,3 Tetramethylbutyl phenol; Phospholipon 90G phosphatidylcholine (zwitterionic charged phospholipid); and IGEPAL CO-890 Polyoxyethylene (40) nonylphenyl ether, branched. The results for natural beeswax are summarized in Table 11, below. The results for synthetic beeswax are summarized in Table 12, below.

TABLE 11

Natural Beeswax

| Surfactant | Average Increase (nm) Over Baseline Relative to Control: 5 Minutes | Average Increase (nm) Over Baseline Relative to Control: 30 Minutes | Average Increase (nm) Over Baseline Relative to Control: 60 Minutes | Average Increase (nm) Over Baseline Relative to Control: 120 Minutes | n |
|---|---|---|---|---|---|
| 90G | 13.55 | 19.64 | 17.14 | 14.57 | 22 |
| CA 897 | 20.46 | 24.00 | 19.35 | 18.03 | 37 |
| CO-890 | 7.00 | 23.80 | 23.00 | 16.20 | 5 |
| DMPG | 28.93 | 31.31 | 28.75 | 25.43 | 79 |

TABLE 12

Synthetic Beeswax

| Surfactant | Average Increase (nm) Over Baseline Relative to Control: 5 Minutes | Average Increase (nm) Over Baseline Relative to Control: 30 Minutes | Average Increase (nm) Over Baseline Relative to Control: 60 Minutes | Average Increase (nm) Over Baseline Relative to Control: 120 Minutes | n |
|---|---|---|---|---|---|
| 90G | 20.27 | 27.20 | 19.60 | 13.47 | 15 |
| CA 897 | 23.50 | 26.00 | 17.50 | 11.00 | 4 |
| DMPG | 21.93 | 20.40 | 9.73 | 8.20 | 5 |

The natural beeswax wax ester and the anionic surfactant DMPG was shown to provide superior results across all time intervals. The natural beeswaxes, in general, were shown to attain and maintain higher average increase in lipid layer thickness after 120 minutes.

Example 4

Particle Size

In order to provide the desired characteristics, the oil and wax ester portion of the ophthalmic suspension should be retained in the ocular environment for an extended period of time. Wax ester particle size is preferably maintained to provide for long lasting lipid layer increases on eye over time.

Particle size was determined utilizing a Microtrac Sync 3R Flow device. Particle size analysis was carried out using samples of about 6.0 mL that may be stored in plastic bottles until testing. Prior to testing, each bottle was shaken 10 times. The entire cap was then removed and approximately two drops of sample were transferred to the Microtrac Sync 3R Flow device using a plastic pipette. The sample was loaded to the particle size analyzer. Approximately two drops (0.060 g) of sample were injected into a 200 mL deionized water circulating chamber and testing was initiated.

Results from mineral oil alone indicated that the loss of added mineral oil does not extend beyond 30 minutes as observed in the competitive product, Systane® Balance. The results are summarized in Table 13.

The processing parameter labeled "Homogenizer" in Table 13 refers to processing by only the homogenizer in the range of from about 10 k to about 18 k rpm for about 4 to about 8 minutes. The other processing parameters refer to the pressure of the micofluidizer system utilized to evaluate homogeneity. This additional processing was added after initial homogenization and resulted in a reduction in particle size but decreased the clinical performance (average increase in over baseline). More specifically, based on particle size analysis conducted on several test formulas, the homogenizer-only process yielded mean particle sizes in the 2 to 20 micron range while samples further processed with a microfluidizer yields mean particle sizes of micron. Actual measurements of the formulations determined the significant range for particle size and distribution. Specifically, formulations with mean particle sizes of about 1 micron do not remain in the eye, while the best-performing formulas had a mean particle size in the 5 to 20 micron range under the conditions of the measurement.

TABLE 13

| Processing Parameter (kpsi) | Average of Mean Particle Size (nm) | Average Increase (nm) Over Baseline Relative to Control: 5 Minutes | Average Increase (nm) Over Baseline Relative to Control: 30 Minutes | Average Increase (nm) Over Baseline Relative to Control: 60 Minutes | Average Increase (nm) Over Baseline Relative to Control: 120 Minutes | N |
|---|---|---|---|---|---|---|
| Homogenizer | 13.6 | 19.2 | 22.1 | 20.7 | 17.4 | 32 |
| 2.5 | 4.7 | 7.9 | 14.4 | 12.5 | 13.1 | 8 |
| 5 | 8.9 | 13.8 | 16.0 | 21.0 | 8.3 | 6 |
| 10 | 2.3 | 2.1 | 21.6 | 14.9 | 6.7 | 7 |
| 15 | 1.7 | −1.3 | 3.5 | 22.3 | 6.8 | 6 |
| 20 | 0.9 | 0.3 | 4.4 | 4.8 | 6.8 | 10 |

Example 5

Ophthalmic Suspension On-Eye Performance

A study was conducted to evaluate the on-eye performance of the ophthalmic suspension as set forth in Table 1. The study yielded positive results both in terms of emulsified suspension properties and on-eye performance. Particularly, studies were conducted on patients who exhibited diminished tear film with low levels of lipid layer thickness (LLT) based on previous and day-of screenings. The thickness of the lipid layer of the tear film at baseline using interferometry was measured. The baseline lipid layer thickness for these patients ranged from 25 nm to 70 nm with an average of 45 nm. A lipid layer thickness of less than 70 nm was considered deficient.

After the baseline measurements were taken, a single test drop of the ophthalmic suspension in Table 1 (of Example 1) and a single control drop were self-instilled in contralateral eyes. The control drop selected was the solution commercially available as Systane® Ultra PF (commercially available, a non-lipid containing drop that is free of preservatives).

With the main objective being an evaluation of increase of lipid layer thickness, the first challenge was to develop a rigorous inclusion and exclusion criteria for patient recruitment to select subjects that had a chronically desiccated tear film due to Evaporative Dry Eye (e.g., Meibomian Gland Dysfunction or MGD), rather than partial blinking or a side effect of another medication or procedure. Primarily, this study sought subjects with a baseline lipid layer thickness of less than 55 nm in at least one eye, and less than 50% partial blinking rate, both measured using the LipiView (Johnson and Johnson). Additionally, patients with elevated risk factors such as other ocular diseases, pregnancy, or recent use of certain drugs were not considered for this evaluation.

Once inclusion criteria were established, a formal protocol for the clinician and staff to follow had to be created. In this document, each step of the patient evaluation process was laid out in a checkbox format; from initial patient evaluation and day-of confirmation of inclusion to the actual evaluation and measurement processes. Each step was documented for the physician and staff to follow sequentially:

1. Inclusion determination
2. Exclusion confirmation
3. Ocular health exam (Evaluation specifics were at the physician's discretion)
4. Baseline LLT reading
5. SPEED Pre-assessment (Standard Patient Evaluation of Eye Dryness), see Korb et al. Lid wiper epitheliopathy and dry eye symptoms. *Eye Contact Lens*. 2005 January; 31(1):2-8; and Korb et al. The effect of two novel lubricant eye drops on tear film lipid layer thickness in subjects with dry eye symptoms. *Optom Vis Sci*. 2005 July; 82(7):594-601, each incorporated by reference with regard to such survey testing.
6. Test and Control Drop Instillation
7. Measurement at 5, 30, 60, 120, 180, and 240-minute time intervals
8. SPEED Post-Assessment The drops were masked to the patients, but not masked for the physician and staff. All study results were recorded on a data record form with patient identity masked.

Over the course of two weeks, 12 patients completed the study. The results, as illustrated in Tables 14 and 15, show the raw average lipid layer thickness readings for the 12 patients measured. The ophthalmic suspension of Table 1 showed a significant increase in lipid layer thickness at the 5 and 30-minute time points. At all-time points, there was significant separation between the ophthalmic suspension and the control drop. The ophthalmic suspension maintained a 72.5 (+/−3.8) nm average lipid layer thickness at the 4-hour mark compared with the control at 61.8 (+/−2.2) nm.

TABLE 14

Ophthalmic Suspension

| Time Interval | Lipid Layer Thickness (nm) |
|---|---|
| Baseline | 49.5 |
| 5 Minutes | 79.2 |
| 30 Minutes | 77.6 |
| 60 Minutes | 70.2 |
| 120 Minutes | 74.0 |
| 180 Minutes | 70.4 |
| 240 Minutes | 72.5 |

TABLE 15

Systane® Ultra

| Time Interval | Lipid Layer Thickness (nm) |
|---|---|
| Baseline | 57.6 |
| 5 Minutes | 66.8 |
| 30 Minutes | 66.2 |
| 60 Minutes | 61.3 |
| 120 Minutes | 61.1 |
| 180 Minutes | 63.5 |
| 240 Minutes | 61.2 |

Based on the raw data from contralateral eyes, differences emerged in the average baseline lipid layer thickness in the test and control eyes. Thus, in addition to using lipid layer thickness at each time point as a key metric, the average increase from baseline in lipid layer thickness across patients with both the test and control drops was evaluated. Table 16 provides the lipid layer thickness increase obtained from the ophthalmic suspension as set forth in Table 1. Table 17 provides the lipid layer thickness increase obtained from the Systane® Ultra PF solution.

Clear separation of the test and control drops at every time point are illustrated, with the ophthalmic suspension showing a nearly 50% increase in lipid layer thickness at the 4-hour mark. Thus, reduction in lipid layer thickness is delayed to well beyond the 4-hour mark before returning to baseline. If the degradation rate remains linear, a significant lipid layer thickness increase is likely to extend well beyond 8 hours using only a single drop of the ophthalmic suspension.

TABLE 16

Ophthalmic Suspension

| Time Interval | Increase In Lipid Layer Thickness (nm) | Percentage Increase in Lipid Layer Thickness |
|---|---|---|
| 5 Minutes | 29.7 | 59.9% |
| 30 Minutes | 28.1 | 56.7% |
| 60 Minutes | 20.7 | 41.8% |
| 120 Minutes | 24.5 | 49.5% |
| 180 Minutes | 20.9 | 42.3% |
| 240 Minutes | 23.0 | 46.5% |

TABLE 17

Systane® Ultra

| Time Interval | Increase In Lipid Layer Thickness (nm) | Percentage Increase in Lipid Layer Thickness |
|---|---|---|
| 5 Minutes | 9.2 | 15.9% |
| 30 Minutes | 8.6 | 14.9% |
| 60 Minutes | 3.7 | 6.4% |
| 120 Minutes | 3.5 | 6.1% |
| 180 Minutes | 5.9 | 10.4% |
| 240 Minutes | 4.2 | 7.4% |

Two subjective questions were asked to patients immediately upon drop instillation for each eye. The first question asked patients to score their initial comfort from 0-100. The second question was to report the duration of any visual blurring they noticed. For the ophthalmic suspension, the average patient noted an 85 out of 100 comfort score and 5.6 seconds of minimal visual blurring. For the control drop the average results were 92 out of 100 and 2.9 seconds. While there is a difference on both metrics between test and control, blurring was less than 3 seconds longer for the ophthalmic suspension, while initial comfort score varied by 7 out of 100.

Most patients reported no blurring for the ophthalmic suspension, with the longest blur duration was 30 seconds (one in test eye and one in control eye). The patient comfort scores were similar and ranged from 45 to 100 in the test eye and 50 to 100 in the control eye. Based on thousands of hours of in-house testing, the comfort and blur are similar to the control solution.

A self-administered SPEED dry eye symptom questionnaire was incorporated into this study. A score of 8 or greater indicated the presence of dry eye. Patients responded with an average SPEED score of 13.58 at the beginning of the test, prior to drop instillation. All patients tested reported initial SPEED scores of greater than 8.

After 4 hours elapsed after drop instillation, patients were re-tested using SPEED. The average result for the post assessment was a score of 10.5, with no patients reporting an increased score and five patients reporting a score of less than 8. The assessment did not distinguish symptoms between eyes. Since the experiment was conducted in contralateral eyes, the delineating effect of the ophthalmic suspension versus the control drops was difficult. The SPEED assessment was meant to gauge symptoms over a span of weeks or months, so an immediate result may not be an accurate reflection of the patient's symptoms. Finally, the time of day was a variable not controlled for in this study and may have had an effect on patient-reported symptoms.

In summary, this study demonstrated a significant increase in lipid layer thickness relative to control over a four-hour interval in an arms-length, physician-administered study. Particularly, the ophthalmic demonstrated a nearly 50% increase in lipid layer thickness at the 4-hour mark in a controlled on-eye patient evaluation thereby resulting in a decrease in patient reported dry eye symptoms. These benefits were observed without significant implications relative to initial drop comfort and visual blurring.

While not being bound to a particularly theory, as wax ester particles are dissolving, the oil bound with the wax ester particles is believed to be released into the tear film and migrates to the surface, continuously replenishing the patient's diminished evaporative lipid barrier. Differently-sized particles dissolve at different rates. In effect, the wide distribution of oil-bound wax ester particles creates a controlled-release mechanism that delivers lipids into the tear film with every blink as the wax ester particle is dissolved. The wax ester is believed to act as a mechanism to slow the lipid layer from draining through the puncta during the course of regular tear turnover.

Example 6

Ophthalmic Suspensions Compared to Commercial Artificial Tears

A study was conducted to evaluate the on-eye performance of the ophthalmic suspension as set forth in Table 1 versus different commercially available artificial tear products (HyloCare®, Tears Again, Cationorm®, Hylovision®, Thealoz®, EvoTears®, TheraTears®, Systane® Complete, Systane® Balance, Soothe®XP, Retaine® MGD and Refresh Optive® Advanced).

Lipid layer thickness measurements of the commercial products were taken out to 60 minutes. The ophthalmic suspension was measured to 120 minutes and beyond. The testing was open-label and utilized Systane Ultra PF® as the control. A total of 93 observations (n=93) among the 12 commercially available products were made. The results show that no product was able to increase lipid layer thickness 13 nm over the control at the 5-minute time interval, and the best performing commercial product showed an increase in 10 nm over control at the 60-minute time interval.

On average, an increase in 21 nm over the control at the 5-minute time interval with the lipid layer thickness continuing to increase to 24.7 nm at the 60-minute time point (n=78). The aggregated data is summarized in Tables 18 and 19.

TABLE 18

| Ophthalmic Suspension (n = 78) | |
|---|---|
| Time Interval | Increase In Lipid Layer Thickness (nm) From Baseline |
| 5 Minutes | 20 |
| 30 Minutes | 24 |
| 60 Minutes | 23 |

TABLE 19

| Commercial Product (n = 93) | |
|---|---|
| Time Interval | Increase In Lipid Layer Thickness (nm) From Baseline |
| 5 Minutes | 5 |
| 30 Minutes | 3 |
| 60 Minutes | 2 |

In aggregate, the ophthalmic suspensions showed a five times (5×) improvement in immediate lipid layer thickness increase over 78 cumulative observations compared with the 93 cumulative observations of the 12 commercially available products. This gap in lipid layer thickness increase is eleven times (11×) at the 60-minute mark with the ophthalmic suspension showing a 23 nm increase over baseline relative to control versus the commercial products only showing a two nm increase over baseline relative to control.

Example 7

Tear Film Stability

A wax ester containing oil-in-water suspension was compared to several other commercially available products.

A beeswax containing ophthalmic suspension: H714: 5.0 Dr-21, 10.0% Bee's Milk (Beeswax, Sesame Oil, Lecithin, Methyl Paraben, and Water) (Koster Keunen), 0.18 Tween-80, 0.1 EDTA, and b.a./NaCl to 100 mOsm.

Water soluble polymer solution #1: *DUASORB* (polymeric system containing 0.1% Dextran 70, 0.3% hydroxypropyl methylcellulose 2910), 0.001% polyquaternium-1, sodium borate, KCl, NaCl, $H_2O$, and HCl and/or NaOH.

Tear film performance was evaluated using the standard contralateral eye experiments by observation of the interference patterns. In terms of method of delivery, a standard full drop of approximately 50 μL was delivered to the eyes of five subjects.

Wax-ester formulation H714 versus to water soluble polymer solution #1: H714 performed very well in the interference analysis of tear film thickness. Initially, H714 scored 2.5 grades above baseline for the first two hours and returning to baseline after three hours. In one set of experiments the water soluble polymer solution, on the other hand, was 2.0 grades above baseline initially but faded quite rapidly within 30 minutes. In another set of experiments, after instillation both the H714 and the water soluble polymer were at about 1.8 grades above baseline. After 15 minutes water soluble polymer solution #1 went virtually back to baseline, while H714 (~1% beeswax) remained on the eye for over two hours. The water soluble polymer #1 which showed an initial a 2.0 score change showed a return to essentially baseline at 1 hour. (see FIG. 2).

Example 8

Zeta Potential and Ionic Mobility Analysis

Zeta potential testing was conducted to evaluate particle performance and stability of various ophthalmic suspensions versus an ophthalmic drop commercially available as Systane® Balance. Zeta potential indicates the degree of electrostatic repulsion between similarly charged particles in a dispersion. In general, a high negative zeta potential correlates to stability (e.g., a dispersion will resist aggregation). In the ophthalmic context, the applicant has demonstrated a higher negative potential directly translates to longer dwell time of an ophthalmic suspension on the eye.

Ionic mobility testing was conducted on the same ophthalmic suspensions and Systane® Balance eye drop to evaluate the particle velocity generated by an electric field.

The content of the ophthalmic suspensions tested (samples A-F) are show in Table 20. Sample A was homogenized at a speed of 10,000 RPM for two minutes with beeswax added into the aqueous phase. Sample B was homogenized at a speed of 20,000 RPM for eight minutes with beeswax added into the aqueous phase. Samples C and D were homogenized at a speed of 18,000 RPM for eight minutes with beeswax added into the aqueous phase. Samples E and F were homogenized at a speed of 18,000 RPM for eight minutes with beeswax added into the oil phase with the oil and water phases separated and tested. The Systane® Balance eye drop included propylene glycol (0.6%) lubricant as the primary active ingredient along with various inactive ingredients including boric acid, dimyristoylphosphatidylglycerol, edetate disodium, hydroxypropyl guar, mineral oil, polyoxyl 40 stearate, POLYQUAD® (polyquaternium-1) 0.001% preservative, sorbitan tristearate, sorbitol and purified water, as well as hydrochloric acid and/or sodium hydroxide to adjust pH.

The results of the zeta potential and ionic mobility testing are provided in Table 21.

TABLE 20

| Component | Weight (% w/w) | | | | | |
|---|---|---|---|---|---|---|
| Sample | A | B | C | D | E | F |
| Water | 91.65 | 91.37 | 91.67 | 91.67 | 91.67 | 91.67 |
| NaCl | 0.67 | 0.55 | 0.55 | 0.55 | 0.55 | 0.55 |
| NaH2PO4 | 0.03 | 0.03 | 0.03 | 0.03 | 0.03 | 0.03 |
| Na2HPO4 | 0.25 | 0.25 | 0.25 | 0.25 | 0.25 | 0.25 |
| Tween-80 | 0.4 | 0.6 | 0.4 | 0.4 | 0.4 | 0.4 |
| DMPG | 0.4 | 0.6 | 0.5 | 0.5 | 0.5 | 0.5 |
| Beeswax | 1 | 1 | 1 | 1 | 1 | 1 |
| HA | 0.1 | 0.1 | 0.1 | 0.1 | 0.1 | 0.1 |
| Drakeol ®-35 | 4.5 | 4.5 | 4.5 | 4.5 | 4.5 | 4.5 |
| Drakeol ®-15 | 1 | 1 | 1 | 1 | 1 | 1 |

TABLE 21

| Sample | ζ Potential (mV) | μ Ionic Mobility (μm/s)/(V/cm) |
|---|---|---|
| A | −76 | −5.9 |
| B | −94 | −7.4 |
| C | −80 | −6.3 |
| D | −93 | −7.2 |
| E | −81 | −6.3 |
| F | −90 | −7.1 |
| Systane ® Balance | −6 | −0.5 |

Ophthalmic suspensions A-F all demonstrated a zeta potential of from about −75 to about −95 and an ionic mobility of from about −6 to about −7.5. These results demonstrate that ophthalmic suspensions as provided herein provide sizable stabilization of large particles as well as sustained thickening of tear film, unlike that of the Systane® Balance eye drop which demonstrated markedly different zeta potential and ionic mobility.

Example 9

Suspension Separation

A preparation of the formula in Table 1 was allowed to stand for a minimum of two hours. The formulation showed separation of the suspension showing different regions as an oil phase to a water phase. The formulation was then stained using solid Oil Red dye which preferentially stains the oil in the formulation which is a hydrocarbon oil but does not stain the wax ester component. Microscopic observation of the phases show the different regions of the separated product including the oil phase that contains mineral oil with discrete unstained wax particles primarily with estimated particle size of 200 to 500 nm with some larger particle greater than two microns. Sample of the preparation were separated into the oil phase and aqueous phase. Each was tested in eyes with the results showing that the particle associated with the oil phase showed the primary activity associated with extension of time that the product enhanced the lipid layer thickness.

Example 10

USP (87) Biological Reactivity
Testing—Benzalkonium Chloride (BAK)

Testing was conducted by a neutral third party laboratory to determine the cytotoxicity of benzalkonium chloride (BAK) when used as a preservative in a standard topical saline ophthalmic solution vehicle. Test solutions of BAK at various dilutions at the typical preservation concentration used in ophthalmic products (50 ppm) were subject to USP (87) biological reactivity testing and graded according to reactivity. All solutions contained EDTA as an adjunct to enable the BAK to be active against gram negative bacteria. All negative and positive controls were nominal. All test solutions were graded as exhibiting "severe" reactivity meaning there was nearly complete destruction of all cell layers and therefore use of BAK did not meet USP requirements. Thus, in conclusion, BAK (with EDTA) at concentrations 5% of the "use concentration" in typical ophthalmic products caused severe reactivity according to the USP (87) biological reactivity test.

It should be understood that the above description is only representative of illustrative embodiments and examples. For the convenience of the reader, the above description has focused on a limited number of representative examples of all possible embodiments, examples that teach the principles of the disclosure. The description has not attempted to exhaustively enumerate all possible variations or even combinations of those variations described. That alternate embodiments may not have been presented for a specific portion of the disclosure, or that further undescribed alternate embodiments may be available for a portion, is not to be considered a disclaimer of those alternate embodiments. One of ordinary skill will appreciate that many of those undescribed embodiments, involve differences in technology and materials rather than differences in the application of the principles of the disclosure. Accordingly, the disclosure is not intended to be limited to less than the scope set forth in the following claims and equivalents.

It is to be understood that, while the disclosure has been described in conjunction with the detailed description, thereof, the foregoing description is intended to illustrate and not limit the scope. Other aspects, advantages, and modifications are within the scope of the claims set forth below.

Generalized Statements of the Disclosure

The following numbered statements provide a general description of the disclosure and are not intended to limit the appended claims.

Statement 1. An ophthalmic suspension is provided that includes: i) an aqueous phase comprising water and one or more components selected from the group consisting of at least one wax ester, at least one anionic polar surfactant, at least one nonionic surfactant, at least one salt, and at least one phosphate; and ii) an oil phase comprising at least one mineral oil and, optionally, at least one wax ester. The wax ester exhibits a mean particle size of at least about 5.0 microns using a Microtrac particle analyzer procedure to determine particle size.

Statement 2. The present disclosure provides an ophthalmic emulsified suspension of Statement 1.

Statement 3. The present disclosure provides an ophthalmic suspension of any of Statements 1-2, wherein the ophthalmic suspension has an osmolality of from about 245 mOsmol/kg to about 315 mOsmol/kg.

Statement 4. The present disclosure provides an ophthalmic suspension of any of Statements 1-3, wherein the ophthalmic suspension is formulated as a free flowing emulsified suspension at about 30° C.

Statement 5. The present disclosure provides an ophthalmic suspension of any of Statements 1-4, wherein the wax ester is present in a concentration of about 0.8 weight percent to about 1.2 weight percent.

Statement 6. The present disclosure provides an ophthalmic suspension of any of Statements 1-5, wherein the wax ester is a natural beeswax.

Statement 7. The present disclosure provides an ophthalmic suspension of any of Statements 1-6, wherein the ophthalmic suspension exhibits a negative zeta potential of from about −60 mV to about −110 mV.

Statement 8. The present disclosure provides an ophthalmic suspension of any of Statements 1-7, wherein the ophthalmic suspension exhibits an ionic mobility of from about −5.9 (μms)/(V/cm) to about −7.4 (μms)/(V/cm).

Statement 9. The present disclosure provides an ophthalmic suspension of any of Statements 1-8, wherein the oil is a mixture of a lightweight mineral oil and a heavy weight mineral oil.

Statement 10. The present disclosure provides an ophthalmic suspension of any of Statements 1-9, wherein the lightweight mineral oil exhibits a kinetic viscosity of from about 3.0 mm$^2$s$^{-1}$ to about 34.4 mm$^2$s$^{-1}$ at 40° C. and the heavy weight mineral oil exhibits a viscosity of kinetic viscosity of from about 34.5 mm$^2$s$^{-1}$ to about 150 mm$^2$s$^{-1}$ at 40° C.

Statement 11. The present disclosure provides an ophthalmic suspension of any of Statements 1-10, further including an anionic polar surfactant comprising a mixture of a polysorbate non-ionic surfactant at a concentration of about 0.35 to about 0.45 weight percent and an anionic polar dimyristoylphosphatidylglycerol at a concentration of about 0.35 to about 0.55 weight percent.

Statement 12. The present disclosure provides an ophthalmic suspension of any of Statements 1-11, packaged in a sterile multi-use or sterile single use container.

Statement 13. The present disclosure provides an ophthalmic suspension of any of Statements 1-12, packaged in a multi-dose non-preserved (MDNP) container or a container including at least one preservative.

Statement 14. The present disclosure provides an ophthalmic suspension of any of Statements 1-13, wherein ophthalmic suspension increases lipid layer thickness by at least 20 nanometers at five minutes after administration.

Statement 15. The present disclosure provides an ophthalmic suspension of any of Statements 1-14, wherein the ophthalmic suspension increases lipid layer thickness by at least 20 nanometers at four hours after administration.

Statement 16. A method of increasing lipid layer thickness is provided and includes the step of administering an ophthalmic suspension of any of Statements 1-15 to an eye of a patient in need of treatment.

Statement 17. The present disclosure provides a method of increasing lipid layer thickness of Statement 16, wherein the lipid layer thickness is increased by at least 20 nm within five minutes of administration.

Statement 18. The present disclosure provides a method of increasing lipid layer thickness of any of Statements 16-17, wherein the lipid layer thickness is increased by at least 20 nm at four hour after administration.

Statement 19. The present disclosure provides a method of lubricating an eye including administering to the eye an ophthalmic suspension of any of Statements 1-15 to an eye of a patient in need of treatment.

Statement 20. The present disclosure provides a method of for alleviating the symptoms of dry eye including administering to the eye an ophthalmic suspension of any of Statements 1-15 to an eye of a patient in need of treatment.

Statement 21. An ophthalmic suspension is provided that includes a wax dispersion including (a) water; (b) at least one oil; (c) a surfactant; and (d) at least one wax ester present in a concentration of about 0.5 to about 1.5 weight percent. The at least one wax ester in the ophthalmic suspension binds a mucin layer, an aqueous layer, and a lipid layer in an eye of a subject and act to maintain or enhance the integrity of an interstitial layer between the mucin layer and the aqueous layer, and interstitial layer between the aqueous layer and the lipid layer.

Statement 22. The present disclosure provides an ophthalmic solution of Statement 21, wherein the at least one wax ester acts to increase the thickness of the mucin layer, the aqueous layer, the lipid layer, or a combination thereof.

Statement 23. The present disclosure provides an ophthalmic suspension of any of Statements 21-22, wherein binding and homeostasis enabled by the wax, wax esters or hydrolysis products allows the mucin layer, the aqueous layer and the lipid layer of a tear film to interact with to each other allowing the tear film to remain on the eye for extended periods of time (e.g., at least two hours).

Statement 24. An ophthalmic suspension is provided that exhibits a zeta potential of from about −60 mV to about −110 mV.

Statement 25. An ophthalmic suspension is provided that forms a meta stable emulsion which separates into an oil phase and a water phase on contact with an eye and provides lubrication for about 2 to about 12 hours on the eye.

Statement 26. A method for alleviating the symptoms of dry eye is provided which includes the step of contacting an eye with an ophthalmic suspension of any of Statements 21-25.

Statement 27. The present disclosure provides a method alleviating the symptoms of dry eye of Statement 26, wherein on contact with an eye the ophthalmic suspension interacts with: a lipid layer; an aqueous layer; a mucin layer; an interface between the lipid layer and the aqueous layer; and an interface between the aqueous layer and the mucin layer of the eye and unprotected corneal cells.

Statement 28. The present disclosure provides a method alleviating the symptoms of dry eye of any of Statements 26-27, where the wax ester of the ophthalmic suspension is a natural beeswax or a synthetic beeswax.

Statement 29. The present disclosure provides a method alleviating the symptoms of dry eye of any of Statements 26-28, wherein the oil is a mixture of a lighter weight mineral oil and a heavier mineral weight oil.

Statement 30. The present disclosure provides a method alleviating the symptoms of dry eye of any of Statements 26-29, wherein the oil is present in a concentration of about 1.0 weight percent to about 5 weight percent.

Statement 31. The present disclosure provides a method alleviating the symptoms of dry eye of any of Statements 26-30, wherein the surfactant is a mixture of two or more surfactants.

Statement 32. The present disclosure provides a method alleviating the symptoms of dry eye of any of Statements 26-31, wherein (i) the oil is a mixture of a lighter weight oil and a heavier weight oil and is present in a concentration of about 1.0 to about 5.5 weight percent; (ii) the surfactant is a mixture of a Polysorbate 80 in a concentration of about 0.35 to about 0.45 weight percent and a dimyristoylphosphatidylglycerol in a concentration of about 0.3 to about 0.5 weight percent; (iii) the wax ester is a natural or a synthetic beeswax present in a concentration of about 0.5 to about 1.0 weight percent; and the ophthalmic suspension has an osmolality of about 245 to about 310 mOsmol/kg.

Statement 33. The present disclosure provides a method alleviating the symptoms of dry eye of any of Statements 26-32, wherein the ophthalmic suspension is packaged in a sterile multi-use or sterile single use container.

Statement 34. The present disclosure provides a method alleviating the symptoms of dry eye of any of Statements 26-33, wherein the ophthalmic suspension is packaged in a multi-dose non-preserved (MDNP) container or a container including at least one preservative.

Statement 35. The present disclosure provides a method of preparing an ophthalmic suspension that includes the steps of: (a) preparing a wax ester and a surfactant in a purified or deionized water suspension; (b) preparing an oil-in-water emulsion comprising an oil in a purified or deionized water suspension; (c) separately autoclaving the beeswax dispersion and the oil-in-water emulsion; (d) and aseptically blending the autoclaved beeswax dispersion and the oil-in-water emulsion so as to prepare the meta stable oil-in-water emulsion ophthalmic suspension.

Statement 36. The present disclosure provides a method of preparing an ophthalmic suspension of Statement 35, wherein the ophthalmic solution provides lubrication for at least about 2 hours on the eye.

Statement 37. The present disclosure provides a method of preparing an ophthalmic suspension of any of Statements 35-36, wherein the ophthalmic solution provides lubrication for at least about 12 hours on the eye.

Statement 38. The present disclosure provides a method of preparing an ophthalmic suspension of any of Statements 35-37, wherein on contact with an eye the ophthalmic suspension penetrates: a lipid layer; an aqueous layer; a mucin layer; an interface between the lipid layer and the aqueous layer; and an interface between the aqueous layer and the mucin layer of the eye and unprotected corneal cells.

Statement 39. The present disclosure provides a method of preparing an ophthalmic suspension of any of Statements 35-38, wherein the wax ester is a natural beeswax.

Statement 40. The present disclosure provides a method of preparing an ophthalmic suspension of any of Statements 35-39, wherein the beeswax is a synthetic beeswax Statement 41. The present disclosure provides a method of preparing an ophthalmic suspension of any of Statements 35-40, wherein the oil is a mixture of a lighter weight oil and a heavier weight oil.

Statement 42. The present disclosure provides a method of preparing an ophthalmic suspension of any of Statements 35-41, wherein the surfactant is a mixture of two or more surfactants.

Statement 43. The present disclosure provides a method of preparing an ophthalmic suspension of any of Statements 35-42, wherein (i) the oil is a mixture of a light weight oil and a heavy weight oil and is present in a concentration of about 1.0 to about 5.5 weight percent; (ii) the surfactant is a mixture of a Polysorbate 80 in a concentration of about 0.35 to about 0.45 weight percent and a dimyristoylphosphatidylglycerol in a concentration of about 0.3 to about 0.5 weight percent; (iii) the wax ester is a natural beeswax or a synthetic beeswax present in a concentration of about 0.25 to about 1.0 weight percent; and the ophthalmic suspension has an osmolality of about 245 to about 310 mOsmol/kg.

Statement 44. The present disclosure provides a method of preparing an ophthalmic suspension of any of Statements 35-43, wherein the ophthalmic suspension is packaged in a sterile multi-use or sterile single use container.

Statement 45. The present disclosure provides a method of preparing an ophthalmic suspension of any of Statements 35-44, wherein the ophthalmic suspension is packaged in a multi-dose non-preserved (MDNP) container or a container including at least one preservative.

Statement 46. The present disclosure provides a method of preparing an ophthalmic suspension of any of Statements 35-44, wherein the ophthalmic suspension is packaged in a container containing a preservative.

Statement 47. The present disclosure provides a method of preparing an ophthalmic suspension of any of Statements 35-46, wherein the wax esters act to increase the thickness of the mucin layer, the aqueous layer, the lipid layer, or a combination thereof.

Statement 48. The present disclosure provides a method of preparing an ophthalmic suspension of any of Statements 35-47, wherein binding and homeostasis enabled by the wax esters allows the mucin layer, the aqueous layer and the lipid layer of a tear film to interact with each other allowing the tear film to remain on the eye for at least two hours.

Statement 49. The present disclosure provides a method of preparing an ophthalmic suspension that includes the steps of: (a) preparing an oil phase; (b) preparing the aqueous phase; (c) mixing the oil phase and aqueous phase to form the ophthalmic suspension; (d) and autoclaving the ophthalmic suspension.

Statement 50. The present disclosure provides a method of preparing an ophthalmic suspension of Statement 49, wherein the step of preparing the oil phase (e.g., heavy weight mineral oil and light weight mineral oil) includes heating to a temperature of from about 63° C. to about 71° C.

Statement 51. The present disclosure provides a method of preparing an ophthalmic suspension of Statements 49-50, wherein the step of preparing the oil phase includes the step of adding or introducing at least one wax ester to the oil phase followed by heating the mixture to a temperature above the melting point of the wax ester (e.g., from about 63° C. to about 71° C.).

Statement 52. The present disclosure provides a method of preparing an ophthalmic suspension of Statements 49-51, wherein the aqueous phase may be prepared by mixing the at least one wax ester, at least one salt, at least one phosphate, at least one surfactant and any other water-soluble ingredient followed by heating the mixture to a temperature above the melting point of the wax ester (e.g., from about 63° C. to about 71° C.).

Statement 53. The present disclosure provides a method of preparing an ophthalmic suspension of Statements 49-52, wherein the individual oil phase and aqueous phase are not separately autoclaved prior to being combined.

Statement 54. The present disclosure provides an ophthalmic suspension consisting of:

a wax dispersion comprising natural beeswax particles, an anionic polar surfactant and water;

sodium hyaluronate; and an oil-in-water emulsion comprising an oil and water; and optionally, at least one preservative selected from the group consisting of polyhexamethylene biguanide, stabilized oxychloro complex and polyquaternium-1, wherein:
(i) the oil is a mixture of a lighter molecular weight mineral oil and a heavier molecular weight mineral oil and is present in a concentration of about 4.0 to about 6.25 weight percent;
(ii) the anionic polar surfactant is a mixture of a Polysorbate 80 in a concentration of about 0.35 to about 0.45 weight percent and an anionic polar dimyristoylphosphatidylglyerol in a concentration of about 0.35 to about 0.50 weight percent; and
(iii) the natural beeswax particles are solid up to about 60° C. and are present in a concentration of about 0.50 to about 1.25 weight percent; and
wherein the ophthalmic suspension vehicle:
(i) forms a meta stable emulsion which separates into an oil phase and a water phase on contact with an eye;
(ii) provides a dwell time on the eye of at least two hours;
(iii) is formulated as a free flowing liquid at room temperature;
(iv) has an osmolality of about 230 mOsmol/kg to about 260 mOsmol/kg; and
(v) has a pH of from about 6.5 to about 7.8.

Statement 55. The present disclosure provides an ophthalmic suspension of Statement 54, wherein the beeswax is present in a concentration of about 1.0 weight percent.

Statement 56. The present disclosure provides an ophthalmic suspension of Statements 54-55, wherein the beeswax is Cera Alba or Cera Flava.

Statement 57. The present disclosure provides an ophthalmic suspension of Statements 1-56, packaged in a sterile single use container.

Statement 58. The present disclosure provides an ophthalmic suspension of Statements 1-56, packaged in a sterile multi-dose container.

Statement 59. The present disclosure provides a finished pharmaceutical product comprising the ophthalmic suspension vehicle of Statements 1-56.

Statement 60. The present disclosure provides a finished pharmaceutical product comprising the ophthalmic suspension vehicle of Statements 1-56.

Statement 61. The present disclosure provides a finished pharmaceutical product comprising the ophthalmic suspension vehicle of Statements 1-56.

What is claimed is:
1. An ophthalmic suspension comprising
   i) an aqueous phase comprising water and one or more components selected from the group consisting of at least one wax ester, at least one anionic polar surfactant, at least one nonionic surfactant, at least one salt, and at least one phosphate; and
   ii) an oil phase comprising at least one mineral oil and, optionally, at least one wax ester,
   wherein the wax ester exhibits a mean particle size of at least about 2.0 microns to about 20.0 microns,
   wherein the ophthalmic suspension increases lipid layer thickness by at least 20 nanometers at 60 minutes after administration.

2. The ophthalmic suspension of claim 1, wherein the ophthalmic suspension has an osmolality of from about 245 mOsmol/kg to about 315 mOsmol/kg.

3. The ophthalmic suspension of claim 1, wherein the ophthalmic suspension is formulated as a free flowing emulsified suspension at about 30° C.

4. The ophthalmic suspension of claim 1, wherein the ophthalmic suspension includes a total wax ester content of about 0.8 weight percent to about 1.2 weight percent.

5. The ophthalmic suspension of claim 1, wherein the ophthalmic suspension exhibits a negative Zeta potential of from about −60 mV to about −110 mV.

6. The ophthalmic suspension of claim 1, wherein the ophthalmic suspension exhibits an ionic mobility of from about −5.9 (μms)/(V/cm) to about −7.4 (μms)/(V/cm).

7. The ophthalmic suspension of claim 1, wherein the oil is a mixture of a lightweight mineral oil and a heavy weight mineral oil.

8. The ophthalmic suspension of claim 7, wherein the lightweight mineral oil exhibits a kinetic viscosity of from about 3.0 mm$^2$s$^{-1}$ to about 34.4 mm$^2$s$^{-1}$ at 40° C. and the heavy weight mineral oil exhibits a viscosity of kinetic viscosity of from about 34.5 mm$^2$s$^{-1}$ to about 150 mm$^2$s$^{-1}$ at 40° C.

9. The ophthalmic suspension of claim 1, further comprising an anionic polar surfactant comprising a mixture of a polysorbate non-ionic surfactant at a concentration of about 0.35 to about 0.45 weight percent and an anionic polar dimyristoylphosphatidylglycerol at a concentration of about 0.35 to about 0.55 weight percent.

10. The ophthalmic suspension of claim 1, packaged in a sterile multi-use or sterile single use container.

11. The ophthalmic suspension of claim 1, packaged in a multi-dose non-preserved (MDNP) container or a container including at least one preservative.

12. The ophthalmic suspension of claim 1, further comprising at least one glycosylaminoglycan.

13. The ophthalmic suspension of claim 12, wherein the glycosylaminoglycan includes hyaluronic acid, a corresponding hyaluronic acid sodium salt, sodium hyaluronate, or any combination thereof.

* * * * *